(12) United States Patent
Nagase et al.

(10) Patent No.: US 6,583,151 B2
(45) Date of Patent: *Jun. 24, 2003

(54) REMEDIES FOR DRUG ADDICTION

(75) Inventors: Hiroshi Nagase, Kamakura (JP);
Takashi Endoh, Chigasaki (JP);
Tsutomu Suzuki, Yokohama (JP);
Kuniaki Kawamura, Kamakura (JP);
Koji Oshima, Yokohama (JP); Hideaki Inada, Kamakura (JP)

(73) Assignee: Toray Industries, Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,364

(22) PCT Filed: Sep. 2, 1998

(86) PCT No.: PCT/JP98/03937
§ 371 (c)(1),
(2), (4) Date: Jul. 12, 1999

(87) PCT Pub. No.: WO99/11289
PCT Pub. Date: Mar. 11, 1999

(65) Prior Publication Data
US 2001/0044449 A1 Nov. 22, 2001

(30) Foreign Application Priority Data
Sep. 2, 1997 (JP) .............................. 9-237426
Sep. 17, 1997 (JP) .............................. 9-252047

(51) Int. Cl.[7] .......................... A61K 31/4748
(52) U.S. Cl. ..................................... 514/289
(58) Field of Search ........................... 514/289

(56) References Cited

FOREIGN PATENT DOCUMENTS

WO          9315081         8/1993

OTHER PUBLICATIONS

Kreek, M. J., Semin. Neurosci., 9(3/4), 140–157 (1997) (abstract).*
Valeri et al., Neuropharmacology, 35(3), 377–384 (1996) (abstract).*
Blake et al., J. Biological Chemistry, 272(2), pp.782–790 (Jan. 10, 1997).*
Kobayashi et al., Drug Dependence. Annual Report, pp. 143–148 (1997) (abstract).*
Kuzumin, Alexander V. et al, European Journal of Pharmacology, Mar. 1997, vol. 321, No. 3, pp.265–271.
Shippenberg, T.S. et al, The Journal of Pharmacology and Experimental Therapeutics, 1996, vol. 276, No. 2, pp.545–554.
Maisonneuve, I.M. et al, Neuroscience Letters, 1994, vol. 181, No. 1–2, pp.57–60.
Heidbreder, Ch. A. et al, Brain Research, 1993, vol. 616, No. 1–2, pp.335–8.
Tsutomu Suzuki et al, Folia Pharmacologica Japonica, Apr. 1997, vol. 109, No. 4, pp. 165–173.
Funada, M. et al, Neuropharmacology, 1993, vol. 32, No. 12, pp. 1315–1323.
Di Chiara, Caetano et al, Proc. Natl. Acad. Sci., USA, 1988, vol. 85, No. 12, pp. 5274–5278.

* cited by examiner

*Primary Examiner*—Phyllis G. Spivack
(74) *Attorney, Agent, or Firm*—Birch, Stewart, Kolasch & Birch, LLP

(57) ABSTRACT

A method for treating drug dependence comprising administering, as the active ingredient, an opioid κ receptor agonist of a compound represented by the following formula, is disclosed (I)

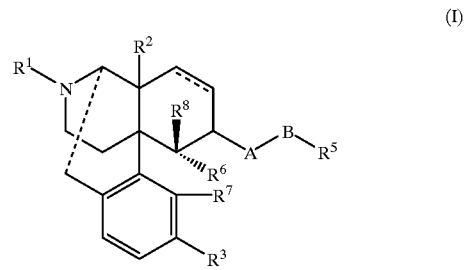

wherein A and the R terms are herein defined.

13 Claims, 11 Drawing Sheets

REMEDIES FOR DRUG ADDICTION

This application is the national phase under 35 U.S.C. §371 of PCT International Application No. PCT/JP98/03937 which has an International filing date of Sep. 2, 1998 which designated the United States of America.

TECHNICAL FIELD

The present invention relates to a remedy for drug dependence. In addition, the present invention relates to a dopamine-release inhibitor, in which dopamine is heavily associated with drug dependence.

BACKGROUND ART

When a person repeatedly take a natural substance such as opium, cocaine, or marijuana, or takes a specific drug such as heroin, barbiturates, or stimulants, it is impossible to suddenly withhold the drug. Then, their major goal in life tends to focus on obtaining these substances and drugs. In addition, brutal crimes may be provoked. Moreover, serious incidents, which affect the state of the nation, may also be provoked. There is substantially the same underlying cause in these problems of drug abuse as in habituation to consuming common substances, for example, alcohol or tobacco.

World Health Organization (WHO) defines both drug dependence and drug abuse. That is, drug dependence is defined as follows: "A state, psychic and sometimes also physical, resulting from the interaction between a living organism and a drug, characterized by behavioural and other responses that always include a compulsion to take the drug on a continuous or periodic basis in order to experience its psychic effects, and sometimes to avoid the discomfort of its absence." Drug dependence is further classified as a state of psychic dependence on a drug, that is, psychic dependence, or a state in which a body is adapted to existing the drug, that is, physical dependence.

The WHO classifies drugs which become addictive into nine groups, that is, 1. alcohol, 2. amphetamines, 3. barbiturates, 4. marijuana, 5. cocaine, 6. hallucinogens, 7. khat, 8. opiates, and 9. organic solvents. All the drugs classified into the nine groups, to which dependence may be developed, also show psychic dependence. In addition, three groups, that is, opiates, barbiturates, and alcohol, may be accompanied by physical dependence. At present, among these drugs which develop dependence, opiates, barbiturates, cocaine, and amphetamines are available for clinical use.

With respect to international laws relevant to dependence-producing drugs, there are the "Single Convention Treaty on Narcotic Drugs" (1961) and the "The Convention on Psychotropic Substances" (1971). Under the above-mentioned two treaties, all countries are to make a concerted effort to conduct strict inspections of international distribution of narcotics and prevent narcotics from being illicitly distributed. As drug abuse expands throughout the world, international regulation becomes stricter. Recently, drugs capable of being abused have increased both in kind and in variety. On the other hand, since exchange of goods and travel have been internationally increased and an information network has been developed, cases of psychotropic drug abuse have increased in addition to cases of narcotics, marijuana, and stimulant abuse. In addition, the drug abuse epidemic area is also spreading throughout the world. For example, recently, narcotics abuse has significantly increased in countries in North America, Central and South America, Southeast Asia, Middle East, and Europe. In particular, the cocaine abuse problem has become a deep social ill in South America, North America, Europe and the like. On the other hand, the stimulants abuse problem has also spread in Japan, North America, and Europe. Furthermore, at present, other psychotropic drug abuses have also increased in these countries.

With respect to a remedy for drug dependence, particular drugs are not usually applied other than drugs used for symptomatic treatment. The main treatment is psychotherapy which is aimed at self-awareness, replacing a dependence-producing drug with a drug which is less dependent, or gradually-decreasing drug treatment. With respect to symptomatic treatment, antianxiety drugs such as diazepam and flunitrazepam, and short-acting barbiturates have been initially used for treatment for acute toxipathy. An antipsychotic agent such as haloperidol or phenotiazines has been used for treatment of acute psychoses. However, the items of concern involve adverse effect such as psychogenesis peculiar to central nervous system sedatives in treatments using drugs such as diazepam, flunitrazepam, or barbiturates. The items of concern involve adverse effects such as psychogenesis peculiar to psychotropic drugs in treatment using drugs such as haloperidol or phenotiazines, so that there is the possibility that drug dependence is replaced by psychotropic drug dependence. (Alcohol and Drug Dependence, Basic Research and Clinical Research, Kenshirou Oohara, Sakutarou Tadokoro (Kaneharasyuppan); Drug Dependence, Mitsumoto Satou, Susumu Fukui (Sekaihokentuusinsya)).

A drug reaction in which after the drug is given to a living organism, drug-seeking behavior or drug-taking behavior are more frequently induced, is defined as a reinforcing effect or a reward effect. These effects caused by the dependence-producing drugs are closely related to an intracerebral dopamine nervous system. The intracerebral dopamine nervous system is roughly classified into two systems, that is, a nigrostriatal system and a mesolimbic system which projects from an ventral tagmental area to a nucleus accumbens. There have been many reports which indicate the reinforcing effect or the reward effect is related to the mesolimbic system.

For example, cocaine, that is a central nervous system stimulant, affects neurosynapses in the nucleus accumbens so as to accelerate dopamine release from dopamine neuroterminals and to inhibit the uptake thereof, so that an amount of dopamine which binds to dopamine receptors increases and nerve activities are facilitated. Therefore, onset of psychic dependence seems to be triggered. On the other hand, since opioid κ receptor agonists inhibit dopamine release in the nucleus accumbens (Japanese Journal of Pharmacology. 109: 165–173, 1997), the opioid κ receptor agonists may suppress the reward effect of cocaine and hold promise as a remedy for psychic cocaine dependence. At present, opioid κ receptor agonists, however, have not been applied in practical use for a remedy for cocaine dependence.

In addition, with respect to the relationship between opiates and their reward effect in drug dependence, it is known that opiates not only have analgesic activity but also function as a chemical mediator for the reward effect. The opioid receptors are classified into $\mu$, $\delta$, and κ receptors. Among them, it was initially reported that $\mu$ receptor agonists such as morphine showed the reward effect (T. Suzuki et al., Eur. J. Pharmacol. 205, 85, 1991). It has been reported that $\mu$ or $\delta$ receptor agonistic endogenous opioid peptides such as β-endorphins and enkephalins also show the reward effect (T. Suzuki et al., Jpn. J. Pharmacol. 66, 131, 1994).

Furthermore, opioid receptors are known to relate to a dopamine nervous system. The opioid μ receptors are distributed in high density in a ventral tegmental area in which cell sonata of the mesolimbic system exist, so that they inhibit an inhibitory γ-aminobutyric acid (GABA) nervous system, that is, interneurons, and stimulate the mesolimbic system. As a result, it is suggested that when a μ receptor agonist is systemically administered or microinjected into the ventral tegmental area, dopamine release in the projected nucleus accumbens seems to be significantly increased. On the other hand, δ, and κ opioid receptors are known to be distributed in high density in the projected area, that is, nucleus accumbens in the mesolimbic system. When δ opioid receptors are activated, similarly to μ opioid receptors, they seem to inhibit the inhibitory GABA nervous system, that is, interneurons, and to facilitate dopamine release in the nucleus accumbens. In contrast, κ receptor agonists do not show the reward effect in a drug self-administration (T. Suzuki et al., Brain Res. 602, 45, 1993). As described above, it is reported that when a κ receptor agonist such as U-50488H which activates κ receptors is administered, dopamine release from the nucleus accumbens is inhibited (Japanese Journal of Pharmacology. 109: 165–177, 1997). In addition, animal tests show that -the reward effect induced by μ or δ receptor agonists is inhibited by κ receptor agonists such as U-50488H (M. Funada et al., Neuropharmacology, 32, 1315, 1993). That is, activation of κ receptors enhances an analgesic effect of μ or δ receptor agonists, but inhibits the reward effect. On the basis of these facts, opioid κ receptor agonists seem to be promising remedies for psychic dependence to opioid μ receptor agonists. Furthermore, it is reported that opioid κ receptor antagonists enhance development of physical dependence, but certain opioid κ receptor agonists inhibit development of physical dependence (Suzuki, T. et al., Eur. J. Pharmacol. 213, 91, 1991). At present, opioid κ receptor agonists, however, have not been adapted to remedies for opioid μ receptor agonists dependence and also have not been applied in practical use.

In a reported case of opioids and nicotine dependence (tobacco addiction), naloxone, that is, a narcotic antagonist (μ receptor antagonist), is effective for a reduction in intake of tobacco of chronic smokers for three hours in a double blind test and a cross-over test with a drug and its placebo (Karras, A. et al., Life Science, 27, 1541, 1980). In contrast, it is reported that naloxone accelerates a withdrawal syndrome in rats with nicotine dependence, and morphine (a μ receptor agonist) inhibits the withdrawal syndrome after an administration of nicotine (Malin, D. H. et al., Psychopharmacology, 112, 339, 1993). In addition, it is reported that nicotinic receptors exist at terminals of a dopamine nervous system in the nucleus accumbens, and relate to facilitation of dopamine release (Di Chiara, G. et al., Natl. Acad. Sci. USA, 85, 5274, 1988). Furthermore, it is reported that a reduction in the amount of dopamine in the nucleus accumbens follows the cessation of the administration of nicotine to rats with nicotine dependence (Fung, Y. K. et al., J. Pharm. Pharmacol., 41, 66, 1989). In contrast, inhibitory activity against nicotine dependence of κ receptor agonists including dynorphin which is an endogenous opioid peptide having κ receptor agonistic activity, particularly inhibitory activity against physical dependence, has not been clear.

In addition, there have been many reports that psychic dependence on a drug such as barbiturates, benzodiazepines which are central nervous system sedatives, amphetamine, methamphetamine, and the like which are stimulants, phencyclidine which is a hallucinogen, and alcohol is controlled by a mechanism of dopamine increase (Yanagita T., Nippon Yakugaku Zasshi—Folia Pharmacologica Japonica. 100 (2): 97–107, 1992 Aug.; Samochowiec J., Annales Academiae Medicae Stetinensis. 40: 195–217 (1994); Kuperman D I. et al., Brain Research. 771 (2): 221–7 (1997); Heron C. et al. European Journal of Pharmacology. 264 (3): 391–8 (1994); Saad S F. et al. Journal of Pharmacy & Pharmacology. 49 (3): 322–8 (1997); Costall B. et al., Arzneimittel-Forschung. 42 (2A): 246–9 (1992)). On the basis of the above-described facts, drugs having activity to inhibit dopamine release from the nucleus accumbens may inhibit the reward effect caused by these dependence-producing drugs and may be a promising remedy for psychic dependence.

In addition, existing highly selective κ receptor agonists such as U-50488H prove not to develop drug dependence which is a characteristic of morphine or the like having reactivity to a μ receptor (T. Suzuki et al., Eur. J. Pharmacol., 205, 85, 1991).

An object of the present invention is to provide a remedy for drug dependence with little adverse effects, which depresses not only onset of psychic dependence but also physical dependence due to controlling the expression mechanism of the reward effect of dependence-producing drugs in a treatment for drug dependence caused by cocaine, opioid μ agonists, nicotine, alcohol, stimulants, barbiturates, benzodiazepines, or hallucinogens. The above-mentioned treatment is different from the conventional symptomatic treatments.

DISCLOSURE OF INVENTION

The present invention provides a remedy for drug dependence in which the active ingredient is an opioid κ receptor agonist. In addition, the present invention also provides a dopamine-release inhibitor in which the active ingredient is an opioid κ receptor agonist.

BEST MODE FOR CARRYING OUT THE INVENTION

Figure 1:
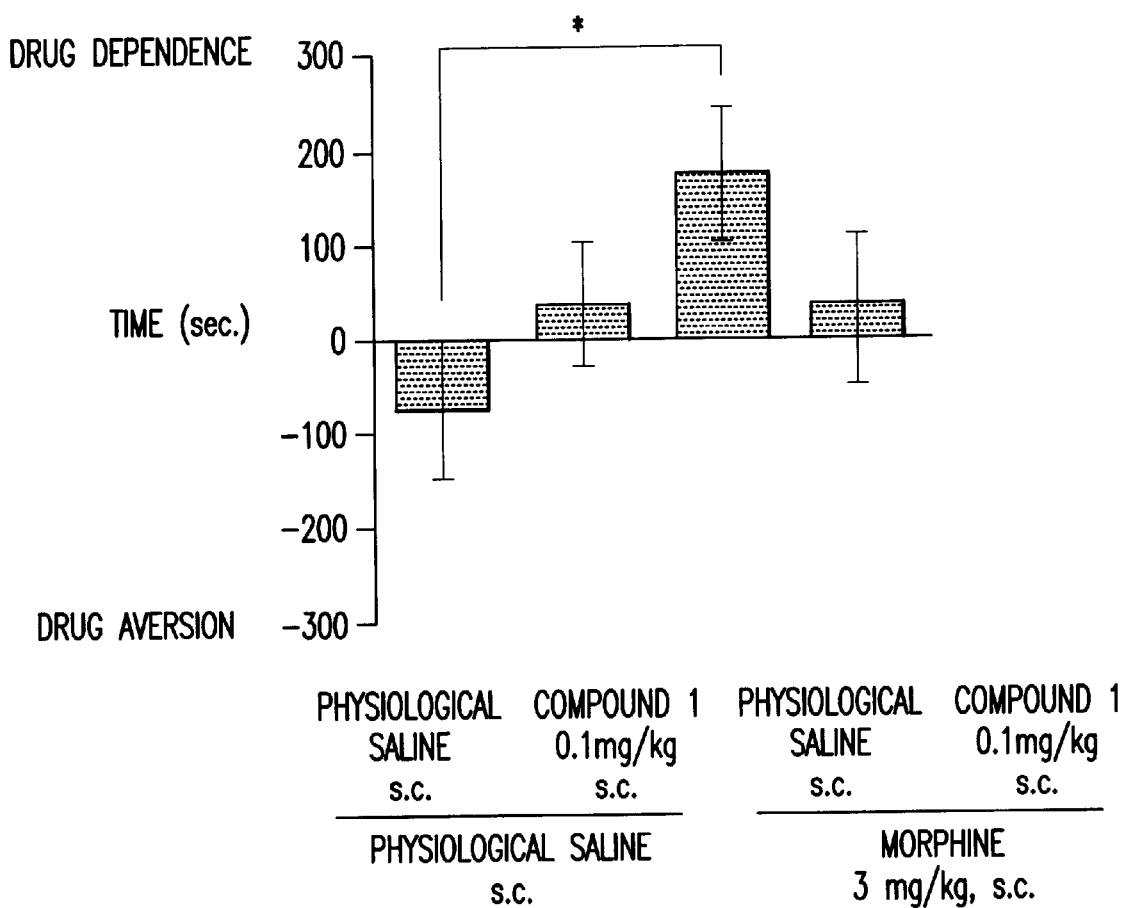
FIG. 1 and FIG. 2 show inhibitory effects of opioid κ receptor agonists against development of psychic dependence induced by an opioid μ receptor agonist.

The present invention includes a remedy for nicotine dependence in which an active ingredient is an opioid κ receptor agonist. In this case, the opioid κ receptor agonist is a compound which is selective towards the opioid κ receptor even if the compound has any specific chemical structure. That is, guinea-pig ileum (GPI) and mouse vas deference (MVD) tests are performed in order to assess agonistic activity on an opioid receptor (assessment of an inhibitory effect on constriction induced by electric stimulation of guinea-pig ileum and mouse vas deference). Then, the same procedure is performed in the presence of an opioid receptor antagonist, in which the antagonist is selective towards μ, δ, or κ receptor, so as to calculate Ke values. When the Ke values of the receptors are compared with each other, a compound, in which Keμ is greater than Keκ and Keδ is simultaneously greater than Keκ, is more selective towards a κ receptor than to a μ and a δ receptor.

Specifically, the compound is an opioid κ receptor agonist or pharmacologically acceptable acid-addition salts thereof represented by the general formula (I):

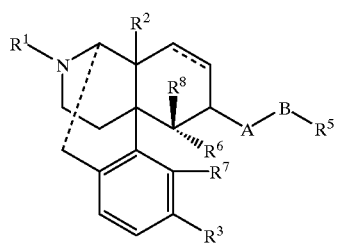

(I)

wherein

----- is a double bond, or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophene-2-ylalkyl group having from 1 to 5 carbon atoms; $R_2$ is a hydrogen atom, a hydroxy group, a nitro group, an alkanoyloxy group having from 1 to 5 carbon atoms, an alkoxy group having from 1 to 5 carbon atoms, an alkyl group having from 1 to 5 carbon atoms, or —$NR^9R^{10}$; $R^9$ is a hydrogen atom or an alkyl group having from 1 to 5 carbon atoms; $R^{10}$ is a hydrogen atom, an alkyl group having from 1 to 5 carbon atoms, or —C(=O)$R^{11}$; $R^{11}$ is a hydrogen atom, a phenyl group, or an alkyl group having from 1 to 5 carbon atoms; $R^3$ is a hydrogen atom, a hydroxy group, an alkanoyloxy group having from 1 to 5 carbon atoms, or an alkoxy group having from 1 to 5 carbon atoms; A is —XC(=Y)—, —XC(=Y)Z-, —X—, or —$XSO_2$— (wherein X, Y and Z are, independently of one another, $NR^4$, S, or O; and $R^4$ is a hydrogen atom, a straight-chain or branched-chain alkyl group having from 1 to 5 carbon atoms, or an aryl group having from 6 to 12 carbon atoms; and $R^4$ may be identical or different in the formula); B is a valence bond, a straight-chain or branched-chain alkylene group having from 1 to 14 carbon atoms (wherein the alkylene group may be substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group, and wherein one to three methylene groups of the alkylene group may be replaced with carbonyl groups), a straight-chain or branched-chain acyclic unsaturated hydrocarbon containing from one to three double bonds and/or triple bonds and having from 2 to 14 carbon atoms (wherein the acyclic unsaturated hydrocarbon may be substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group, and wherein one to three methylene groups of the acyclic unsaturated hydrocarbon maybe replaced with carbonyl groups), or a straight-chain or branched-chain saturated or unsaturated hydrocarbon containing from one to five thioether, ether, and/or amino bonds and having from 1 to 14 carbon atoms (wherein no hetero atoms are bonded directly to A, and one to three methylene groups of the hydrocarbon may be replaced with carbonyl groups); and $R^5$ is a hydrogen atom or an organic group having a basic skeleton selected from the group consisting of the following formulas:

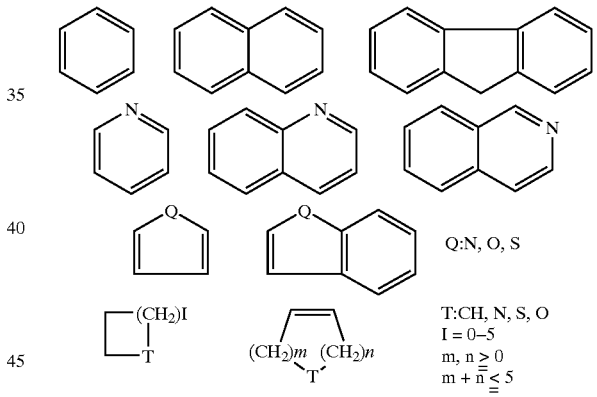

Organic Groups Represented by $R^5$ wherein the organic group may have at least one substituent selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; $R^6$ is a hydrogen atom; $R^7$ is a hydrogen atom, a hydroxy group, an alkoxy group having from 1 to 5 carbon atoms, or an alkanoyloxy group having from 1 to 5 carbon atoms, or $R^6$ and $R^7$ are —O—, —$CH_2$—, —S— together; $R^8$ is a hydrogen atom, an alkyl group having from 1 to 5 carbon atoms or an alkanoyl group having from 1 to 5 carbon atoms. And optionally the compound is an opioid κ receptor agonist or pharmacologically acceptable acid-addition salts thereof represented by the general formula (II):

(II)

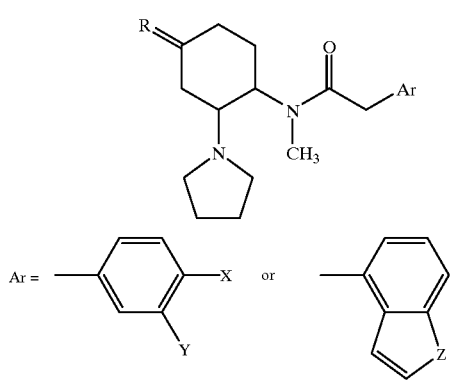

wherein R denotes two hydrogen atoms, or —O—CH$_2$CH$_2$CH$_2$—; X and Y are, independently of each other, a hydrogen atom or a chlorine atom; Z is O or S. And optionally the compound is an opioid κ receptor agonist or pharmacologically acceptable acid-addition salts thereof represented by the general formula (III):

(III)

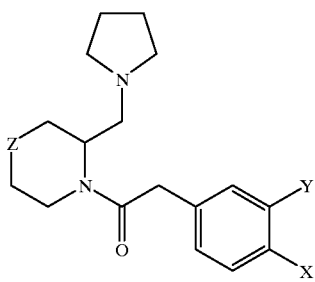

wherein X is a hydrogen atom, a chlorine atom, or a trifluoromethyl group; Y is a hydrogen atom or a chlorine atom; Z is CH$_2$, —OCH$_2$CH$_2$O—, or NCO$_2$CH$_3$. And optionally the compound is an opioid κ receptor agonist or pharmacologically acceptable acid-addition salts thereof represented by the general formula (IV):

(IV)

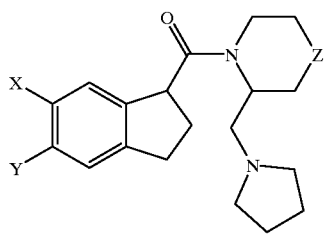

wherein X and Y are, independently of each other, a hydrogen atom or a chlorine atom; Z is CH$_2$, O or S. And optionally the compound is an opioid κ receptor agonist or pharmacologically acceptable acid-addition salts thereof represented by the general formula (V):

(V)

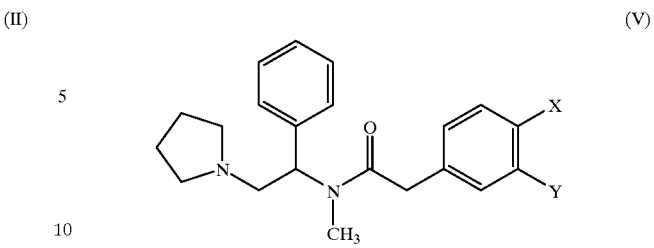

wherein X and Y are, independently of each other, a hydrogen atom or a chlorine atom.

In addition, the present invention includes a remedy for nicotine dependence, a remedy for cocaine dependence, a remedy for opioid μ receptor agonist dependence, and a dopamine-release inhibitor in-which the active ingredient is an opioid κ receptor agonist or pharmacologically acceptable acid-addition salts thereof represented by the general formula (I):

(I)

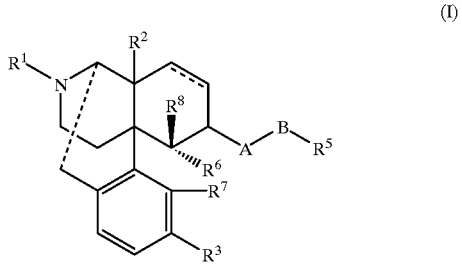

wherein $-----$ is a double bond, or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophene-2-ylalkyl group having from 1 to 5 carbon atoms; $R^2$ is a hydrogen atom, a hydroxy group, a nitro group, an alkanoyloxy group having from 1 to 5 carbon atoms, an alkoxy group having from 1 to 5 carbon atoms, an alkyl group having from 1 to 5 carbon atoms, or —NR$^9$R$^{10}$; $R^9$ is a hydrogen atom or an alkyl group having from 1 to 5 carbon atoms; $R^{10}$ is a hydrogen atom, an alkyl group having from 1 to 5 carbon atoms, or —C(=O)R$^{11}$; $R^{11}$ is a hydrogen atom, a phenyl group, or an alkyl group having from 1 to 5 carbon atoms; $R^3$ is a hydrogen atom, a hydroxy group, an alkanoyloxy group having from 1 to 5 carbon atoms, or an alkoxy group having from 1 to 5 carbon atoms; A is —XC(=Y)—, —XC(=Y)Z—, —X—, or —XSO$_2$— (wherein X, Y and Z are, independently of one another, NR$^4$, S, or O; and $R^4$ is a hydrogen atom, a straight-chain or branched-chain alkyl group having from 1 to 5 carbon atoms, or an aryl group having from 6 to 12 carbon atoms; and $R^4$ may be identical or different in the formula); B is a valence bond, a straight-chain or branched-chain alkylene group having from 1 to 14 carbon atoms (wherein the alkylene group may be substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group, and wherein one to three methylene groups of the alkylene group may be replaced with carbonyl groups), a straight-chain or branched-chain acyclic unsaturated hydrocarbon containing from one to three double bonds and/or triple bonds and having from 2 to 14 carbon atoms (wherein the acyclic unsaturated hydrocarbon may be substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group, and wherein one to three methylene groups of the acyclic unsaturated hydrocarbon may be replaced with carbonyl groups), or a straight-chain or branched-chain saturated or unsaturated hydrocarbon containing from one to five thioether, ether, and/or amino bonds and having from 1 to 14 carbon atoms (wherein no hetero atoms are bonded directly to A, and one to three methylene groups of the hydrocarbon may be replaced with carbonyl groups); and $R^5$ is a hydrogen atom or an organic group having a basic skeleton selected from the group consisting of the following formulas:

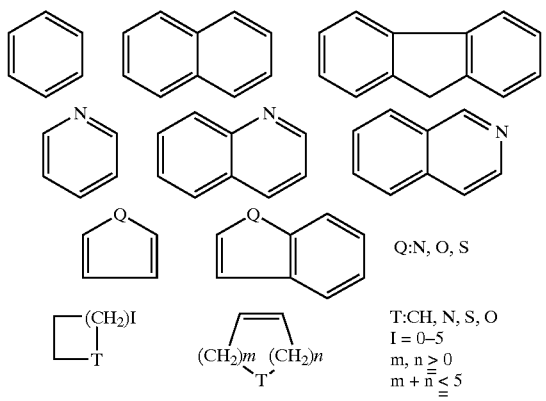

Organic Groups Represented by $R^5$ wherein the organic group may have at least one substituent selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; $R^6$ is a hydrogen atom; $R^7$ is a hydrogen atom, a hydroxy group, an alkoxy group having from 1 to 5 carbon atoms, or an alkanoyloxy group having from 1 to 5 carbon atoms, or $R^6$ and $R^7$ are —O—, —CH$_2$—, —S— together; $R^8$ is a hydrogen atom, an alkyl group having from 1 to 5 carbon atoms or an alkanoyl group having from 1 to 5 carbon atoms.

In the compound represented by the general formula (I) among the κ receptor agonists in accordance with the present invention, $R^1$ is preferably an alkyl group having from 1 to 5 carbon atoms, a cycloalkylmethyl group having from 4 to 7 carbon atoms, a cycloalkenylmethyl group having 5 to 7 carbon atoms, a phenylalkyl group having from 7 to 13 carbon atoms, an alkenyl group having from 4 to 7 carbon atoms, an allyl group, a furan-2-yl-alkyl group having from 1 to 5 carbon atoms, or a thiophene-2-yl-alkyl group having from 1 to 5 carbon atoms; and $R^1$ is particularly preferably a methyl group, an ethyl group, a propyl group, a butyl group, an isobutyl group, a cyclopropylmethyl group, an allyl group, a benzyl group, or a phenethyl group.

$R^2$ is preferably a hydrogen atom, a hydroxy group, a nitro group, an acetoxy group, a methoxy group, a methyl group, an ethyl group, a propyl group, an amino group, a dimethylamino group, an acetylamino group, or a benzoylamino group; and $R^2$ is particularly preferably a hydrogen atom, a hydroxy group, an acetoxy group, or a methoxy group.

$R^3$ is preferably a hydrogen atom, a hydroxy group, an acetoxy group, or a methoxy group, and is particularly preferably a hydroxy group, an acetoxy group, or a methoxy group.

A is preferably —XC(=Y)— (wherein X is $NR^4$, S, or O; Y is O; and $R^4$ is a hydrogen atom, or a straight-chain or branched-chain alkyl group having from 1 to 5 carbon atoms), —XC—(=Y)Z—, —X—, or —XSO$_2$— (wherein X is $NR^4$; Y is O or S; Z is $NR^4$ or O; and $R^4$ is a hydrogen atom, or a straight-chain or branched-chain alkyl group having from 1 to 5 carbon atoms). Specifically, A is —$NR^4$C(=O)—, —$NR^4$C(=S)—, —$NR^4$C(=O)O—, —$NR^4$C(=O) $NR^4$—, —$NR^4$C(=S) $NR^4$—, —$NR^4$C(=O)S—, —OC(=O)—, —OC(=O)O—, —SC(=O)—, —$NR^4$—, —O—, —$NR^4$SO$_2$—, —OSO$_2$— or the like. Among them, A is preferably —$NR^4$C(=O)—, —$NR^4$C(=S)—, —$NR^4$C(=O)O—, —$NR^4$C(=O)$NR^4$—, —$NR^4$C (=S)$NR^4$—, or —$NR^4$SO$_2$—; and more preferably —$NR^4$C(=O)— or —$NR^4$C(=O)O—.

$R^4$ is preferably a hydrogen atom, or a straight-chain or branched-chain alkyl group having from 1 to 5 carbon atoms, and is particularly preferably a straight-chain or branched-chain alkyl group having from 1 to 5 carbon atoms, with a methyl group, an ethyl group, a propyl group, a butyl group or an isobutyl group being the most preferred.

B is preferably a straight-chain alkylene group having from 1 to 10 carbon atoms, —(CH$_2$)$_n$—C(=O)— (n=1 to 4), —CH=CH— (CH$_2$)$_n$— (n=0 to 4), —C≡C—(CH$_2$)$_n$ (n=0 to 4), —CH$_2$—O—, —CH$_2$—S—, —(CH$_2$)$_2$—O—CH$_2$—, or —CH=CH—CH=CH—(CH$_2$)n- (n=0 to 4), and more preferably a straight-chain alkylene group having from 1 to 3 carbon atoms, —CH=CH—, —C≡C—, —CH$_2$—O— or —CH$_2$—S—, with a straight-chain alkylene group having from 1 to 3 carbon atoms, —CH=CH—, or —C≡C— being most preferable.

$R^5$ is preferably a hydrogen atom or an organic group having any one of the following fundamental structures:

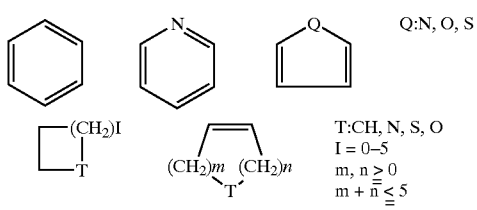

Organic Groups Represented by $R^5$ wherein the organic group may be substituted by a substituents selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an amino group, a nitro group, a cyano group, a isothiocyanato group, a trifluoromethyl group, a trifluoromethoxygroup, and a methylenedioxy group. Among them, a hydrogen atom, a phenyl group, 4-methylphenyl, 3-methylphenyl, 2-methylphenyl, 3,4-dimethylphenyl, 3,5-dimethylphenyl, 4-methoxyphenyl, 3-methoxyphenyl, 2-methoxyphenyl, 3,4-dimethoxyphenyl, 4-hydroxyphenyl, 3-hydroxyphenyl, 3,4-dihydroxyphenyl, 4-fluorophenyl, 3-fluorophenyl, 2-fluorophenyl, 3,4-difluorophenyl, perfluorophenyl, 4-chlorophenyl, 3-chlorophenyl, 2-chlorophenyl, 3,4-dichlorophenyl, 2,4-dichlorophenyl, 2,4,5-trichlorqphenyl, 2,4,6-trichlorophenyl, 4-bromophenyl, 3-bromophenyl, 2-bromophenyl, 4-nitrophenyl, 3-nitrophenyl, 2-nitrophenyl, 4-aminophenyl, 3-aminophenyl, 2-aminophenyl, 4-trifluoromethylphenyl, 3-trifluoromethylphenyl, 2-trifluoromethylphenyl, 4-trifluoromethoxyphenyl, 3-trifluoromethoxyphenyl, 2-trifluoromethoxyphenyl, 3,4-methylenedioxyphenyl, 3-furanyl, 2-furanyl, 3-thienyl, 2-thienyl, cyclopentyl or cyclohexyl are particularly preferred. Of course $R^5$ is not limited to these. These opiate κ receptor agonists represented by the general formula (I) can be produced, for example, by the method disclosed in Japanese Patent No.2525552.

Among the κ receptor agonists in accordance with the present invention represented by the general formula (II), preferred are trans-2-(3,4-dichlorophenyl)-N-methyl-N-[2-(1-pyrrolidinyl) cyclohexyl] acetamide; trans-N-methyl-N-[2-(1-pyrrolidinyl) cyclohexyl] benzo [b] thiophene-4-acetamide; (5β, 7β, 8α)-3,4-dichloro-N-methyl-N-[7-(1-pyrrolidinyl)-1 -oxaspiro [4,5] dec-8-yl] benzeneacetamide; (5β, 7β, 8α)-N-methyl-N-[7-(1-pyrrolidinyl)-1-oxaspiro [4,5] dec-8-yl] benzo [b] furan-4-acetamide; and (5β, 7β, 8α)-N-methyl-N-[7-(1-pyrrolidinyl)-1-oxaspiro [4,5] dec-8-yl] benzeneacetamide. The κ receptor agonists represented by the general formula (II) can be produced, for example, by the methods according to Szmuszkovicz, J. et al., J. Med. Chem., 25, 1125 (1982); Horwell, D. C., et al., U.S. Patent Appl., 558737 (1983); Szmuszkovicz, J. et al., Eur. Patent Appl., EP126612 (1984); Halfpenny, P. R., et al., J. Med. Chem., 33, 286 (1990); or the like.

Among the κ receptor agonists in accordance with the present invention represented by the general formula (III), preferred are methyl 4-[(3,4-dichlorophenyl) acetyl]-3-[(1-pyrrolidinyl) methyl]-1-piperazinecarboxylate; 1-[(4-trifluoromethylphenyl) acetyl]-2-[(1-pyrrolidinyl) methyl] piperidine; 1-[(3,4-dichlorophenyl) acetyl]-2-[(1-pyrrolidinyl) methyl] piperidine; and 1-[(3,4-dichlorophenyl) acetyl]-4,4-ethylenedioxy-2[(1-pyrrolidinyl) methyl] piperidine. The κ receptor agonists represented by the general formula (III) can be produced by the methods according to Naylor, A., et al., J. Med. Chem., 36, 2075 (1993); Vecchietti, V., et al., J. Med. Chem., 34, 397 (1991); Eur. Patent Appl. EP232612 (1987), EP260041 (1988), EP275696 (1988); Scopes, D.I.C., et al., J. Med. Chem., 35, 409 (1992) or the like.

Among the κ receptor agonists in accordance with the present invention represented by the general formula (IV), preferred are 3-(1-pyrrolidinylmethyl)-4-[5,6-dichloro-1-indanecarbonyl]-tetrahydro-1,4-thiazine. These κ receptor agonists represented by the general formula (IV) can be produced, for example, by the method disclosed in WO 94/05646.

Among the κ receptor agonists in accordance with the present invention represented by the general formula (V), preferred are 2-(3,4-dichlorophenyl)-N-methyl-N-[1-phenyl-2 -(1-pyrrodinyl) ethyl] acetamide. These κ receptor agonists represented by the general formula (V) can be produced, for example, by the method according to Barlow, J. J., et al., J. Med. Chem., 34, 3149(1991).

Among the pharmacologically acceptable acid-addition salts of the opioid κ receptor agonists described above are inorganic acid salts, such as hydrochlorides, sulfates, nitrates, hydrobromides, hydroiodides, and phosphates; organic carboxylates, such as acetates, lactates, citrates, oxalates, glutarates, malates, tartrates, fumarates, mandelates, maleates, benzoates, and phthalates; and organic sulfonates, such as methanesulfonates, ethanesulfonates, benzenesulfonates, p-toluenesulfonates, and camphorsulfonates. Among them, hydrochlorides, hydrobromides, phosphates, tartrates, and methanesulfonates are preferred, but of course they are not limited to those compounds.

The opioid κ receptor agonists in accordance with the present invention inhibit dopamine release from the dopamine nervous system in the mesolimbic system which projects from a ventral tagmental area to the nucleus accumbens, so that they are useful as dopamine-release inhibitors. Dopamine is closely related with drug dependence. Dependence-producing drugs such as cocaine; opioid μ agonists; nicotine; alcohol; stimulants; central nervous system sedatives, for example, barbiturates, benzodiazepines, and the like; and hallucinogens induce a reward effect due to an increase in dopamine release from the dopamine nervous system in the mesolimbic system, so that the onset of drug dependence is triggered. Therefore, the opioid κ receptor agonists in accordance with the present invention are useful for treating drug dependence induced by drugs which facilitate dopamine release.

The drug dependence dealt by the present invention represents psychic dependence and physical dependence induced by dependence-producing drugs. Examples of the diseases which can be treated by the remedy in accordance with the present invention are cocaine dependence, opioid μ receptor agonist dependence, nicotine (tobacco) dependence, alcohol dependence, stimulant dependence, central nervous system sedative dependence, and hallcinogen dependence.

Examples of drugs which induce the above-mentioned drug dependences are opioid μ receptor agonists such as morphine, heroin, and codeine; stimulants such as amphetamine and methamphetamine; central nervous system sedatives such as the barbiturates, for example, phenobarbital, pentobarbital, thiopental, and the like, and the benzodiazepines, for example, diazepam, lorazepam, oxazepam, chlordiazepoxide, and the like; and hallucinogens such as phencyclidine. Of course, however, they are not limited to those compounds.

Therapeutic effects of the opioid κ receptor agonists in accordance with the present invention against drug dependence can be assessed by a conditioned place preference method (a CPP method) and a drug discrimination test which are used for assessing psychic dependence, assessment a withdrawal syndrome due to administration of an antagonist which is used as a method for assessing physical dependence, or the like (Suzuki, T. et al., Psychopharmacology, 102, 438–442 (1990); Spyraki, C., The psychopharmacology of dependence, p96, Oxford Medical Publications, New York (1988); Yanagita, T., Psychopharmacology, 27, 503 (1975); Deueau, G. A. et al., Psychopharmacology, 16, 30 (1969); Tsutomu Suzuki, Molecular Medicine, 32, 140 (1995); Maldonado, R. et al., J. Pharmacol. Exp. Ther., 261, 669 (1992)). A significant inhibitory effect on psychic dependence and physical dependence has been confirmed by these tests.

After the opioid κ receptor agonists in accordance with the present invention have been purified to yield a purity which is appropriate for medical use and have passed the required safety tests, they can be orally or parenterally administered without additives or as medical compositions including known pharmacologically acceptable acids, carriers, vehicles, and the like.

With respect to parenterally administered composition, the compounds in accordance with the present invention can be administered using a liquid carrier such as sterilized water without pyrogens, sterilized ethyl oleate without peroxides, anhydrous alcohol, polypropylene glycol, and mixtures thereof, which can be usually used for injection.

Pharmaceutical adjuvants suitable for an injection solution can include stabilizers, solubilizers, buffers, viscosity modifiers, and antioxidants. Examples of these adjuvants are ethanol, ethylenediaminetetraacetic acid (EDTA), tartrate buffers, citrate buffers, and polyethylene oxide viscosity modifiers. These pharmaceutical preparations can be intramuscularly, intraperitoneally, or intravenously injected.

The compounds in accordance with the present invention can be orally administered as solid or liquid pharmaceutical compositions accompanied with a conventional solid or liquid compatible carrier. The pharmaceutical composition which is orally administered can include binders such as syrups, acacia gum, gelatin, sorbitol, tragacanth gum, polyvinyl pyrrolidone, or mixtures thereof, that is, conventional ingredients may be used, Furthermore, the composition can include fillers such as lactose, mannitol, starch, calcium phosphate, sorbitol, methyl cellulose, or mixtures thereof.

In addition, the orally administrated composition can include lubricants such as magnesium stearate, high molecular weight polymers such as polyethylene glycol, high molecular weight fatty acids such as stearic acid, silica or additives such as starch, which facilitate disintegration of solid pharmaceutical preparations, and lubricants such as sulfuric acid lauryl sodium.

The orally administrated composition can be prepared as any conventional forms such as tablets, capsules, lozenges, aqueous or oil suspensions, emulsions, or powders which can be reconstituted using water or other proper solutions before use.

Solid or liquid constituents can include flavors, sweeteners and/or preservatives such as alkyl p-hydroxy benzoate. The liquid constituents can, furthermore, include suspensions such as sorbitol, glucose, other sugar syrups, methyl cellulose, hydroxymethyl cellulose, carboxymethyl cellulose, or gelatin; emulsifiers such as lecithin or sorbitol monooleate; or a usual thickening agent. The liquid constitutents can be, for example, encapsulated in a gelatin capsule.

The pharmaceutical composition in accordance with the present invention is most preferably available in units. In the above-mentioned constitution, the pharmaceutical preparation is subdivided into unit dosages having an adequate dose of an active ingredient. A available unit constitution can be prepared as a packaged pharmaceutical preparation having a package which includes a non-homogenized dose of the pharmaceutical preparation. The package may have constitution such as tablets, capsules, powders, vials, or ampoules. The available unit constitution may be capsules, cachets, tablets, pharmaceutical composition as such, or optionally and properly packaged constitution thereof.

The dosage is properly selected according to symptoms, age, body weight, and administration route. In adults, the daily dosage ranges from 0.001 mg to 1 g as an active ingredient, when it is injected, and the daily dosage ranges from 0.005 mg to 3 g, when it is orally administered. In each case, the dosage can be administered once a day or several times a day.

EXAMPLES

The present invention is described in further detail below with reference to examples.

Example 1

Inhibitory effects of opioid κ receptor agonists against development of psychic dependence induced by an opioid μ receptor agonist.

Inhibitory effects of the opioid κ receptor agonists against development of psychic dependence induced by an opioid μ receptor agonist were examined by a conditioned place preference method (Suzuki, T. et al., Psychopharmacology, 102, 438–442 (1990); Spyraki, C., The psychopharmacology of dependence, p96, Oxford Medical Publications, New York (1988); hereinafter referred to as a CPP method). Morphine was used as the opioid μ receptor agonist which developed psychic dependence. On the other hand, 17-(cyclopropylmethyl)-3,14β-dihydroxy-4,5α-epoxy-6β-[N-methyl-3-(4-trifluoromethylphenyl)propiolamide] morphinan maleate (Compound 1) and 17-(cyclopropylmethyl)-3,14β-dihydroxy-4,5α-epoxy-6β-(N-methyl-3-methylcinnamide) morphinan hydrochloride (Compound 2) were used as the opioid κ receptor selective agonists.

Compound 1

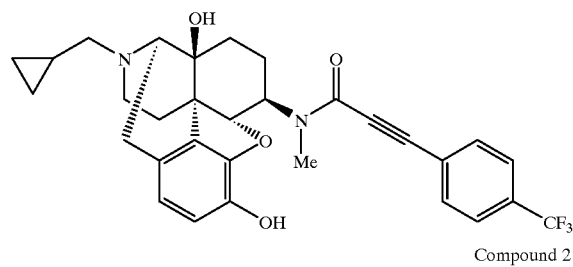

Compound 2

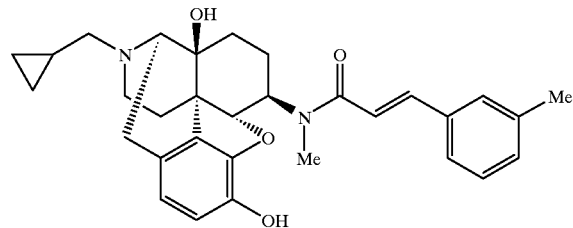

Animals used were Sprague Dawley strain (SD strain) male rats in this experiment. Experiments used were CPP operant boxes having two compartments colored white and black, respectively. In this experiment, animals were given conditioning training for a sensation effect on a drug and environments in the operant boxes (white and black) for six days. After the period for the conditioning training, tests were carried out by placing the conditioned animals in the operant boxes without administration of the drug. Drug dependence and drug aversion were assessed from the periods in which the rats remained in the white or black box during the test.

Figure 2:
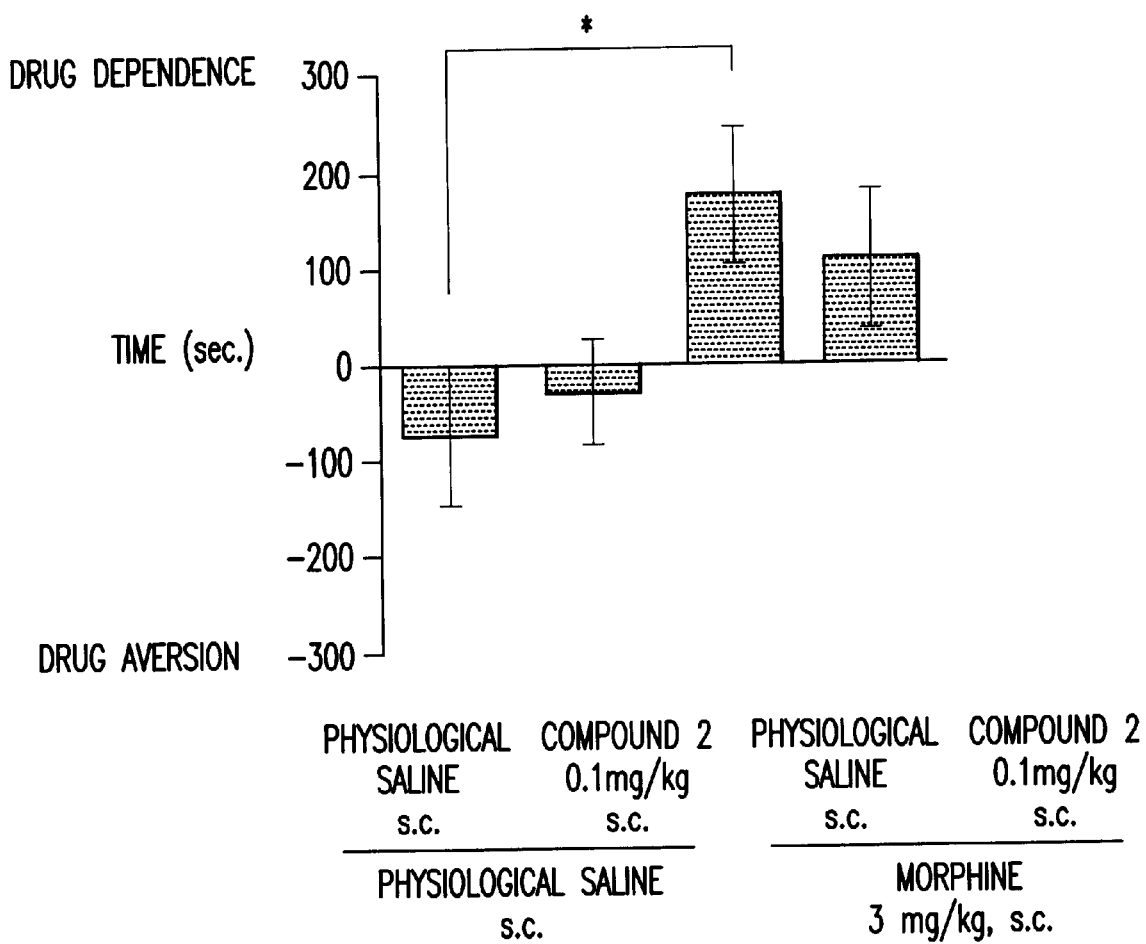

Accordingly, as shown in FIGS. 1 and 2, the periods, in which the rats remained in the box conditioned by the drug, with administration of morphine alone (3 mg/kg, subcutaneously administration) was significantly prolonged compared with a control group to which the solvent was administered. Therefore, development of dependence was recognized. In contrast, it was recognized that the periods in which the rats remained was not significantly prolonged in the test groups which were given morphine in combination with Compound 1 or Compound 2 compared with the control group. Therefore, it was clear that Compound 1 and Compound 2 inhibited the development of drug dependence caused by morphine, when they were subcutaneously given 0.1 mg/kg, respectively. In addition, it was recognized that the periods in which the rats remained of the group given Compound 1 alone or that of Compound 2 alone was not prolonged both in the drug-conditioned box and in the solvent-conditioned box compared with the control group to which the solvent was administered. Therefore, it was clear that these compounds did not develop psychic dependence and aversion.

In addition, in FIGS. 1 and 2, a symbol * represents a level of significance of not more than 5%, thereby indicating statistical significance.

Example 2

Inhibitory effects of an opioid κ receptor agonist against development of psychic dependence induced by an opioid μ receptor agonist, and a result of an antagonism test on an opioid κ receptor antagonist.

Inhibitory effects of the opioid κ receptor agonist against development of psychic dependence induced by an opioid μ receptor agonist were examined by a CPP method (Suzuki, T. et al., Psychopharmacology, 102, 438–442 (1990); Spyraki, C., The psychopharmacology of dependence, p96, Oxford Medical Publications, New York (1988)). Morphine was used as the opioid μ receptor agonist which developed psychic dependence. On the other hand, 17-(cyclopropylmethyl)-3,14β-dihydroxy-4,5α-epoxy-6β-[N-methyl-trans-3-(3-furyl)acrylamide] morphinan hydrochloride (Compound 3) was used as the opioid κ receptor selective agonist. The same experimental procedure was performed as that in Example 1.

Compound 3

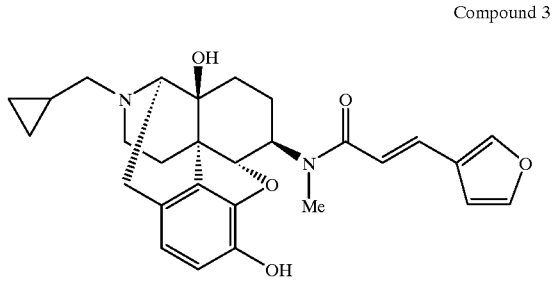

Figure 3:
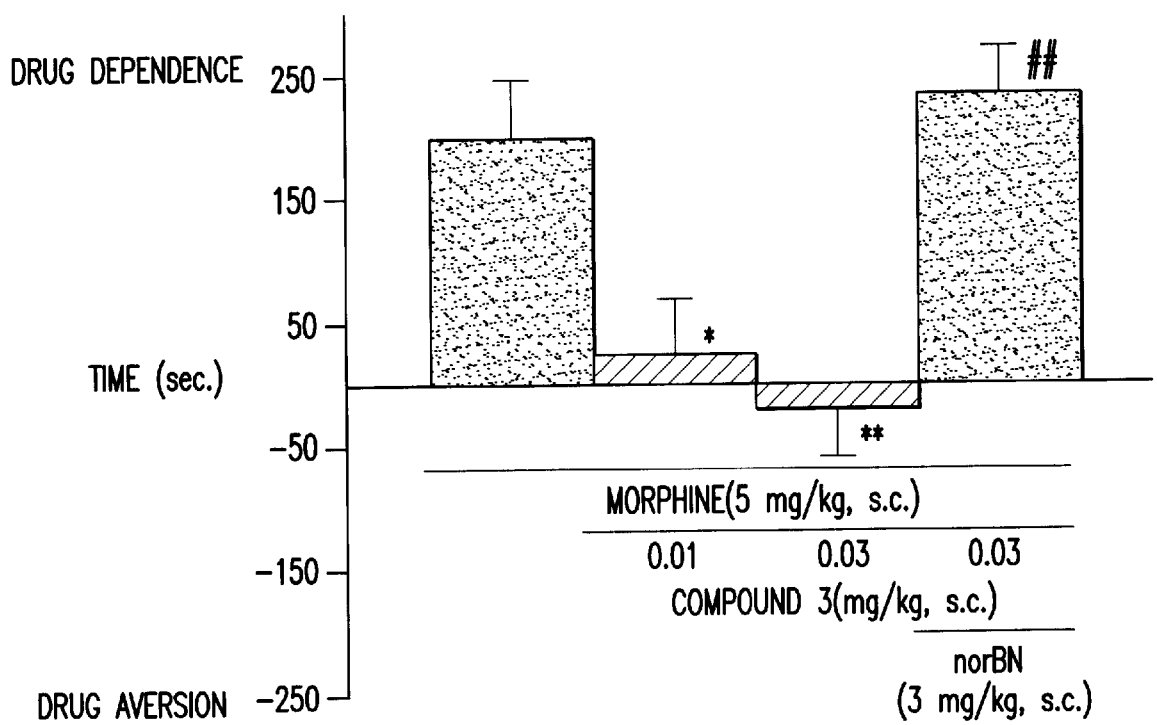
FIG. 3 shows inhibitory effects of an opioid κ receptor agonist against development of psychic dependence induced by an opioid μ receptor agonist, and a result of an antagonism test on an opioid κ receptor atagonist.

Accordingly, as shown in FIG. 3, the periods in which the rats remained in the box conditioned by the drug was significantly prolonged due to the administration of morphine alone (5 mg/kg, subcutaneously administration). Therefore, development of dependence was recognized. In contrast, it was recognized that the periods in which the rats remained was significantly reduced in the test groups which were given morphine in combination with Compound 3 compared with the group to which morphine alone was administered. Therefore, it was clear that Compound 3 inhibited the development of drug dependence caused by morphine, when they were subcutaneously given 0.01 or 0.03 mg/kg of Compound 3, respectively. Furthermore, the inhibitory effect caused by Compound 3 was significantly antagonized by pretreatment with norbinaltorphimine (nor-BNI) (3 mg/kg), that is, an opioid κ receptor selective antagonist, so that it was clear that the inhibitory effect caused by Compound 3 on drug dependence was mediated by the opioid κ receptor.

In addition, it was recognized that the periods in which the rats remained in the group given Compound 3 alone was not prolonged both in the drug-conditioned box and in the solvent-conditioned box compared with the control group to which the solvent was administered. Therefore, it was clear that the Compound 3 did not produce psychic dependence and aversion.

In FIG. 3, a symbol * represents a level of significance of not more than 5%, and a symbol ** represents a level of significance of not more than 1% with respect to the morphine alone treated group (5 mg/kg, subcutaneously administration), thereby indicating statistical significance. Furthermore, a symbol ## represents a level of significance of not more than 1% with respect to the morphine (5 mg/kg, subcutaneously administration) in combination with Compound 3 (0.03 mg/kg, subcutaneously administration) treated group, thereby indicating statistical significance.

Example 3

Effects of an opioid κ receptor agonist on a naloxone-induced withdrawal syndrome (a weight reduction).

Inhibitory effects of the opioid κ receptor agonist on development of physical dependence induced by an opioid μ receptor agonist were examined (Tsutomu Suzuki, Molecular Medicine, 32, 140 (1995); Maldonado, R. et al., J. Pharmacol. Exp. Ther., 261, 669 (1992)). Morphine was used as the opioid μ receptor agonist which developed physical dependence. On the other hand, 17-(cyclopropylmethyl)-3,14β-dihydroxy-4,5α-epoxy-6β-[N-methyl-trans-3-(3 -furyl)acrylamide] morphinan hydrochloride (Compound 3) was used as the opioid κ receptor selective agonist.

Animals used were ddY strain male mouse. Physical dependence was developed using an injection method. Morphine was repeatedly and subcutaneously administered to the mouse twice a day for five days at a dose ranging from 8 to 45 mg/kg, the dose being gradually increased. Naloxone (3 mg/kg) was subcutaneously administered two hours after the last administration of morphine. Then, just after the administration of naloxone, a withdrawal syndrome was observed for 60 minutes. Compound 3 was simultaneously administered with morphine.

Figure 4:
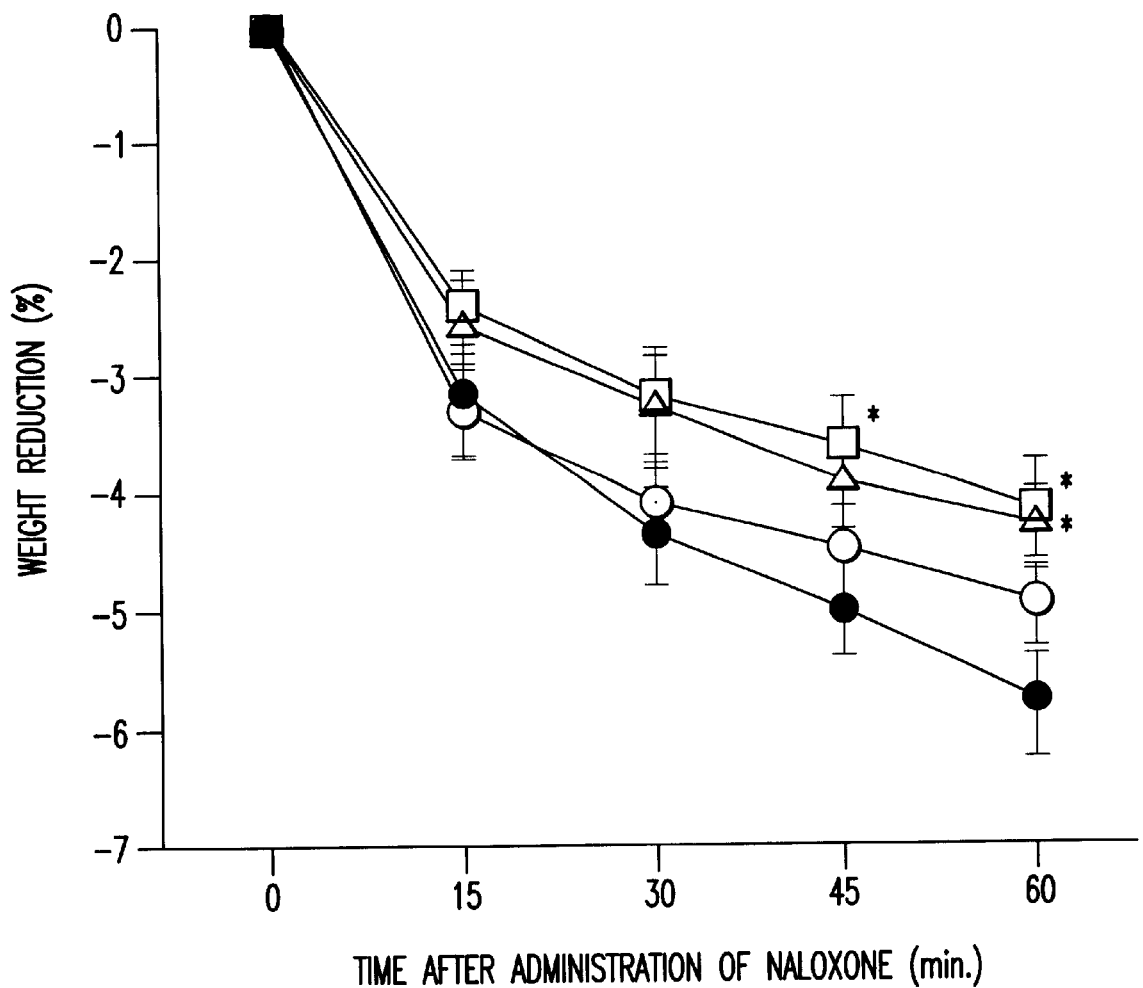
FIG. 4 shows effects of an opioid κ receptor agonist on a naloxone-induced withdrawal syndrome (a weight reduction).

Accordingly, as shown in FIG. 4 and Table 1, the withdrawal syndrome was recognized in the mouse, to which morphine alone was administered, because of the naloxone administration. Therefore, it was confirmed that physical dependence-was developed by morphine. The withdrawal syndrome was relieved by the simultaneous administration of Compound 3 in a dose-dependent manner. Incidence rates of jumping, shaking, and diarrhea were significantly decreased by administration of Compound 3 at a dose of 0.03 mg/kg compared with the group to which morphine alone was administered. In addition, it was recognized that both Compound 3 groups administered at a dose of 0.01 or 0.03 mg/kg revealed significant suppression of body weight reduction compared with the morphine alone administered group. This result showed that the opioid κ receptor agonist inhibited development of physical dependence induced by the opioid µ receptor agonist.

TABLE 1

Effects of an opioid κ receptor agonist on a withdrawalsyndrome induced by naloxone

| Withdrawal syndrome | Physiological saline | Compound 3 (mg/kg, s.c.) | | |
|---|---|---|---|---|
| | | 0.003 | 0.01 | 0.03 |
| Jumping | 10/10 | 3/10 | 5/10 | 3/10* |
| Wobbling | 10/10 | 7/10 | 5/10 | 3/10* |
| Rearing | 10/10 | 10/10 | 7/10 | 8/10 |
| Diarrhea | 10/10 | 7/10 | 6/10 | 3/10* |
| Blepharoptosis | 10/10 | 10/10 | 10/10 | 10/10 |
| Fore paw tremor | 10/10 | 9/10 | 10/10 | 7/10 |

Numbers of mouse manifesting withdrawal syndrome/ Numbers of total mouse

In FIG. 4, a symbol ● represents the group which was given morphine alone, a symbol ○ represents the group which was given morphine in combination with Compound 3 (0.003 mg/kg, subcutaneously administration), a symbol Δ represents the group which was given morphine in combination with Compound 3 (0.01 mg/kg, subcutaneously administration), and a symbol □ represents the group which was given morphine in combination with Compound 3 (0.03 mg/kg, subcutaneously administration). A symbol * represents a level of significance of not more than 5%, thereby indicating statistical significance.

Example 4

Inhibitory effects of opioid κ receptor agonists on development of psychic dependence induced by cocaine.

Inhibitory effects of the opioid κ receptor agonists on development of psychic dependence induced by cocaine were examined by a CPP method (Suzuki, T. et al., Psychopharmacology, 102, 438–442 (1990); Spyraki, C., The psychopharmacology of dependence, p96, Oxford Medical Publications, New York (1988)). 17-(cyclopropylmethyl)-3,14β-dihydroxy-4,5α-epoxy-6β-[N-methyl-3-(3-methylphenyl)propiolamide] morphinan hydrochloride (Compound 4) and 17-(cyclopropylmethyl)-3,14β-dihydroxy-4,5α-epoxy-6β-[N-methyl-trans-3-(methoxycinnamide) morphinan tartrate (Compound 5) were used as the opioid κ receptor selective agonists.

Compound 4

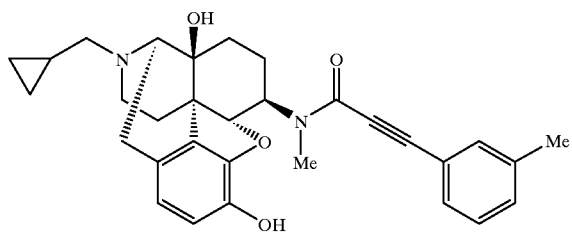

Compound 5

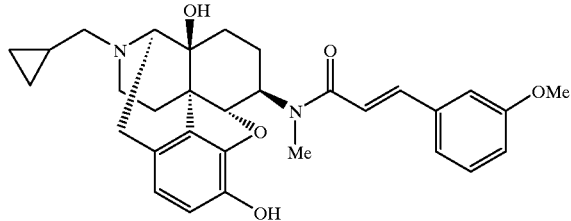

Animals used were Sprague Dawley strain (SD strain) male rats in this experiment. Experiments used were CPP operant boxes having two compartments colored white and black, respectively. In this experiment, animals were given conditioning training for a sensation effect on a drug and environments in the operant boxes (white and black) for six days. After the period for the conditioning training, tests were carried out by placing the conditioned animals in the operant boxes without administration of the drug. Drug dependence and drug aversion were assessed from the periods in which the rats remained in the white or black box during the test.

Figure 5:
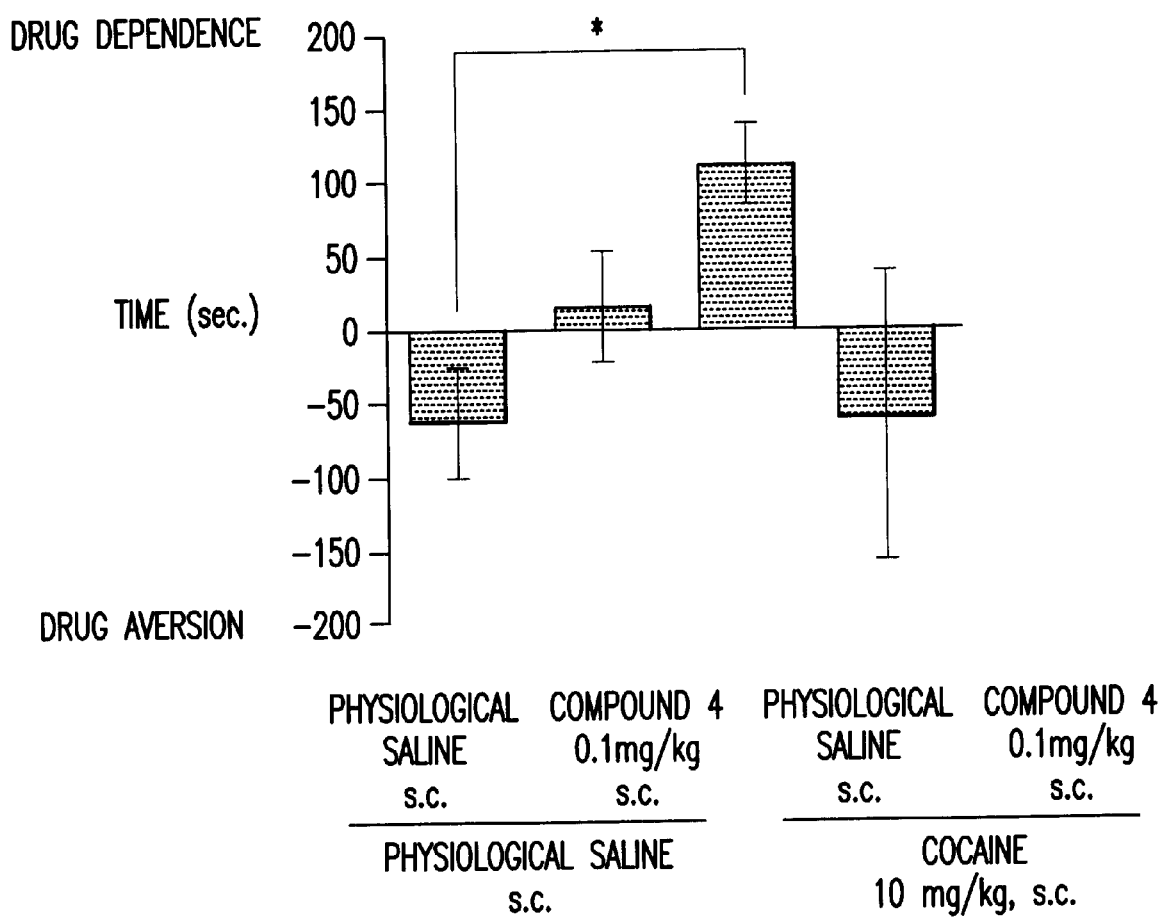
FIG. 5 and FIG. 6 show inhibitory effects of opioid κ receptor agonists against development of psychic dependence induced by cocaine.
Figure 6:
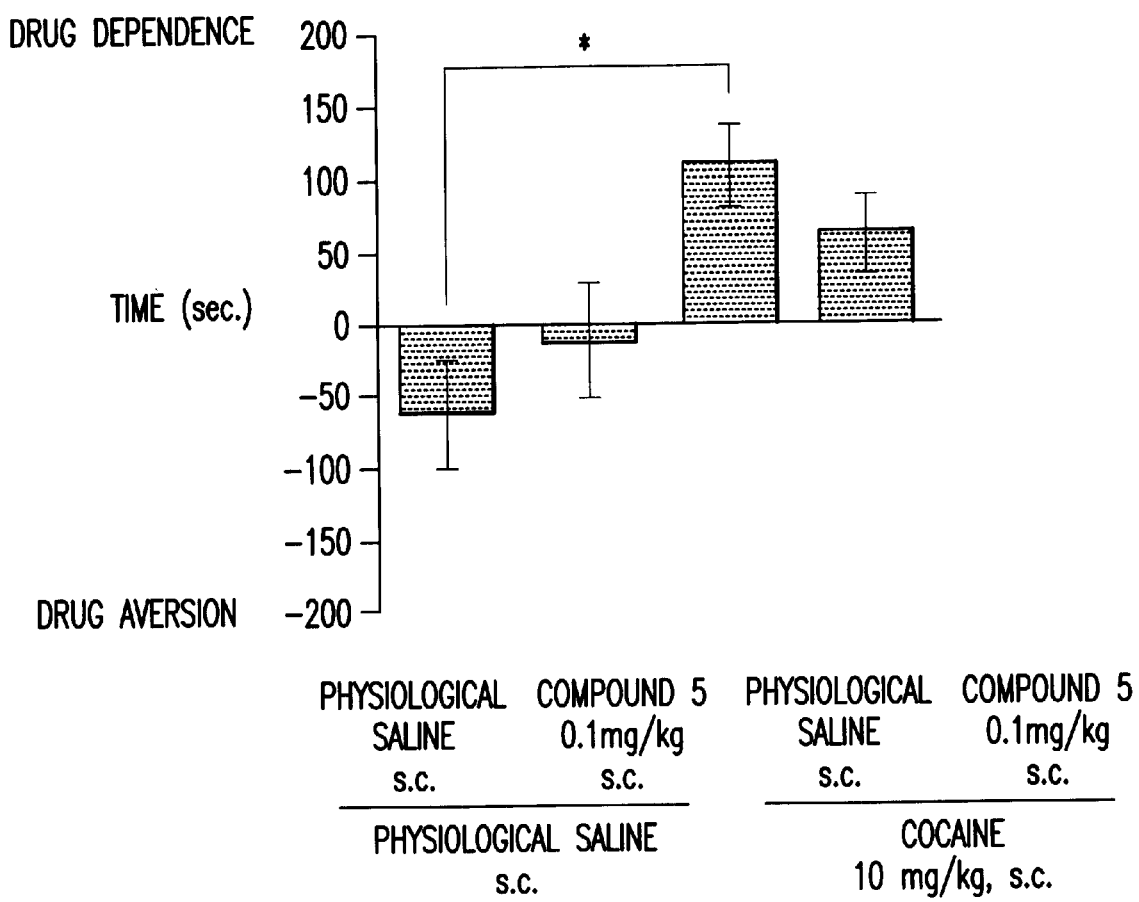

Accordingly, as shown in FIGS. 5 and 6, the periods, in which the rats remained in the box conditioned by the drug, in the group administered cocaine alone (10 mg/kg, intraperitoneal administration) was significantly prolonged compared with that in a control group to which the solvent was administered. Therefore, development of dependence was recognized. In contrast, it was recognized that the periods in which the rats remained was not significantly prolonged in the test groups which were given cocaine in combination with Compound 4 or Compound 5 compared with that in the control group which was given solvent. Therefore, it was clear that Compound 4 and Compound 5 inhibited the development of drug dependence induced by cocaine, when they were subcutaneously given 0.1 mg/kg of Compound 4 and Compound 5, respectively. In addition, it was recognized that the periods in which the rats remained in the group given Compound 4 alone or that of Compound 5 alone was not prolonged both in the drug-conditioned box and in the solvent-conditioned box. Therefore, it was clear that these compounds did not produce psychic dependence and aversion.

In addition, in FIGS. 5 and 6, a symbol * represents a level of significance of not more than 5%, thereby indicating statistical significance.

Example 5

Inhibitory effects of an opioid κ receptor agonist on development of psychic dependence induced by cocaine.

Inhibitory effects of the opioid κ receptor agonist on development of psychic dependence induced by cocaine was examined by a CPP method (Suzuki, T. et al., Psychopharmacology, 102, 438–442 (1990); Spyraki, C., The psychopharmacology of dependence, p96, Oxford Medical Publications, New York (1988)). 17-(cyclopropylmethyl)-3,14β-dihydroxy-4,5α-epoxy-6β-[N-methyl-3-(4-trifluoromethylphenyl)propiolamide] morphinan maleate (Compound 1) was used as the opioid κ receptor selective agonist. The same experimental procedure was performed as that in Example 4.

Figure 7:
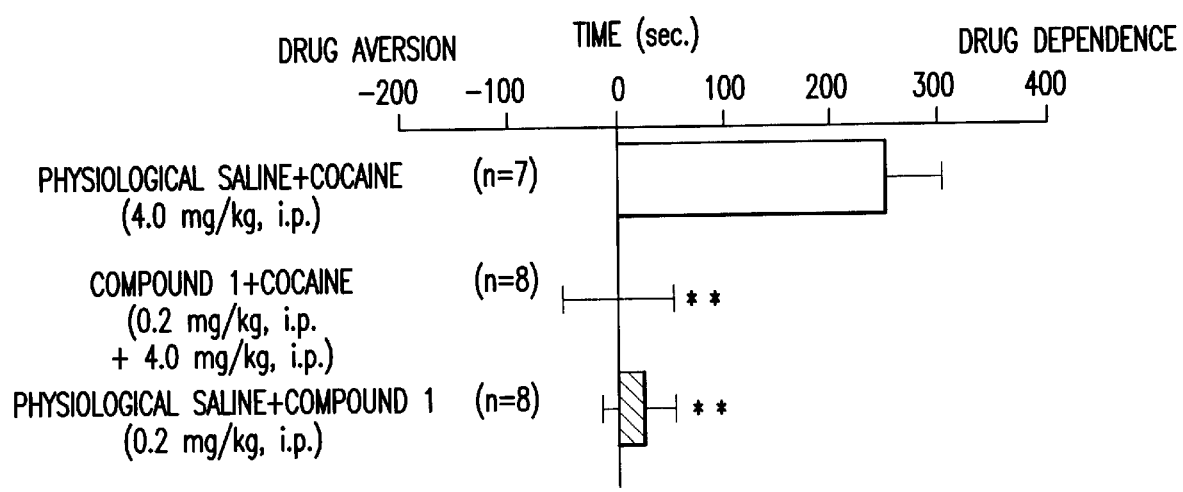
FIG. 7 shows inhibitory effects of an opioid κ receptor agonist against development of psychic dependence induced by cocaine.

Accordingly, as shown in FIG. 7, the periods, in which the rats remained in the box conditioned by the drug, in the group administered cocaine alone (4 mg/kg, intraperitoneal administration) was significantly prolonged, so that development of dependence was recognized. In contrast, it was recognized that the period in which the animals remained was significantly decreased in the test group which were given cocaine in combination with Compound 1 compared with that in the control group which was given cocaine alone. Therefore, it was clear that Compound 1 inhibited the development of drug dependence induced by cocaine, when it was intraperitoneally given 0.2 mg/kg.

In addition, it was recognized that the period in which the rats remained in the group given Compound 1 alone was not prolonged both in the drug-conditioned box and in the solvent-conditioned box compared with that in the control group which was given solvent. Therefore, it was clear that the compound did not produce psychic dependence and aversion.

In addition, in FIG. 7, a symbol ** represents a level of significance of not more than 1%, thereby indicating statistical significance.

Example 6

Inhibitory effect of opioid κ receptor agonist on a drug discrimination test.

Rats were preliminarily trained for the drug discrimination test (Yanagita, T., Psychopharmacology, 27, 503 (1975); Deueau, G. A. et al., Psychopharmacology, 16, 30 (1969)) by previously giving cocaine at a dose of 10 mg/kg or physiological saline, in which an indicator is feeding behavior with lever pressing. 17-(cyclopropylmethyl)-3,14β-dihydroxy-4,5α-epoxy-6β-[N-methyl-trans-3-(3-furyl) acrylamide] morphinan hydrochloride (Compound 3), that, is, an opioid κ receptor selective agonist (10 μg/kg) was administered in combination with cocaine (each dose) to the rats, so that the drug discrimination test was performed.

Figure 8:
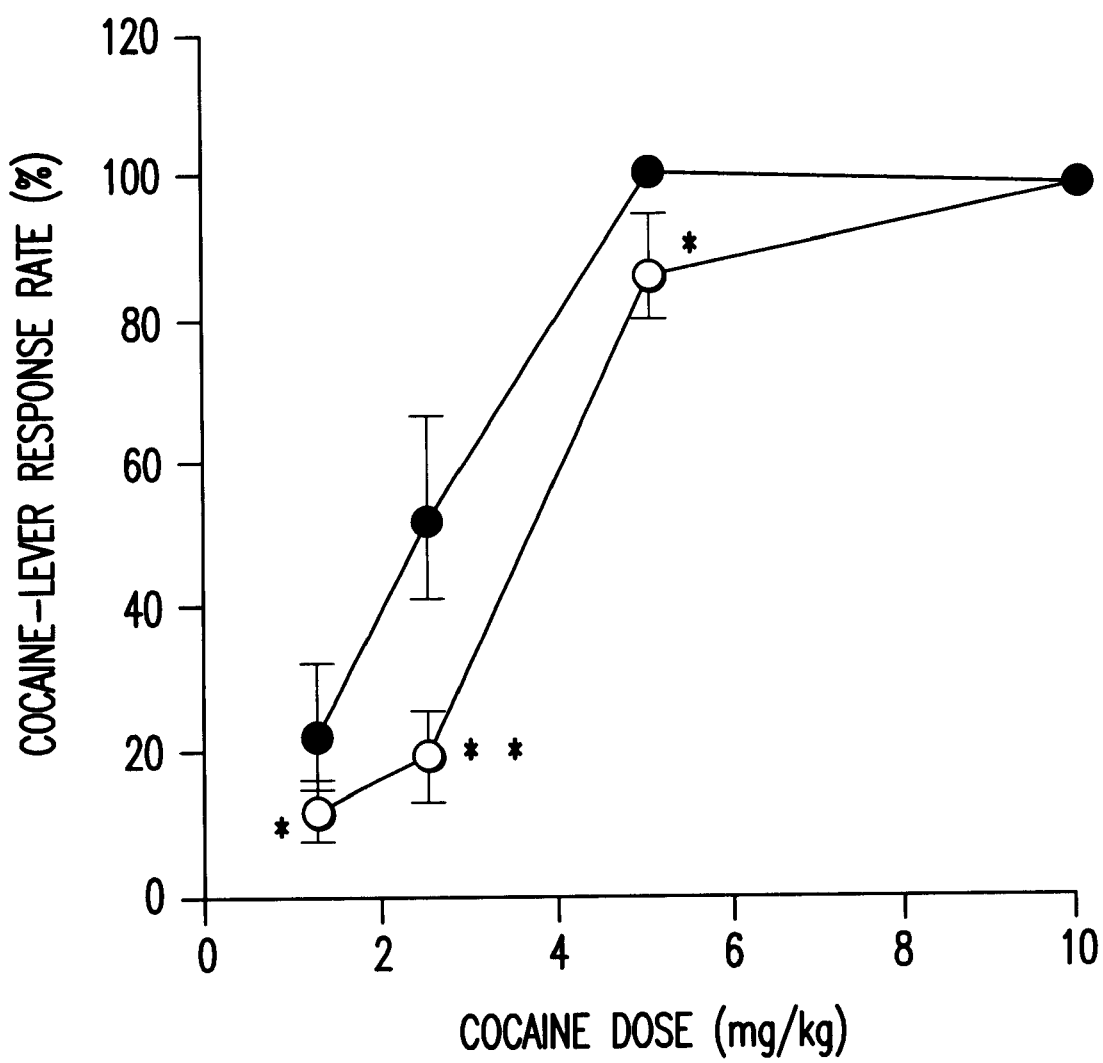
FIG. 8 shows a drug discrimination effect of opioid κ receptor agonist.

The results are shown in FIG. 8. Rates of feeding behavior with lever pressing were significantly decreased in the groups which were administered cocaine at a dose of 1.25, 2.5, or 5 mg/kg in combination with Compound 3 compared with that in the solvent control group which was administered cocaine in combination with physiological saline. Accordingly, it was revealed that Compound 3 inhibited manifestation of a reward effect induced by cocaine, so that Compound 3 is suggested to be a promising remedy for cocaine dependence.

In FIG. 8, a symbol ● represents the group which was given physiological saline in combination with cocaine, and a symbol ○ represents the group which was given Compound 3 (0.01 mg/kg) in combination with cocaine. A symbol * represents a level of significance of not more than 5%, thereby indicating statistical significance.

Figure 9:
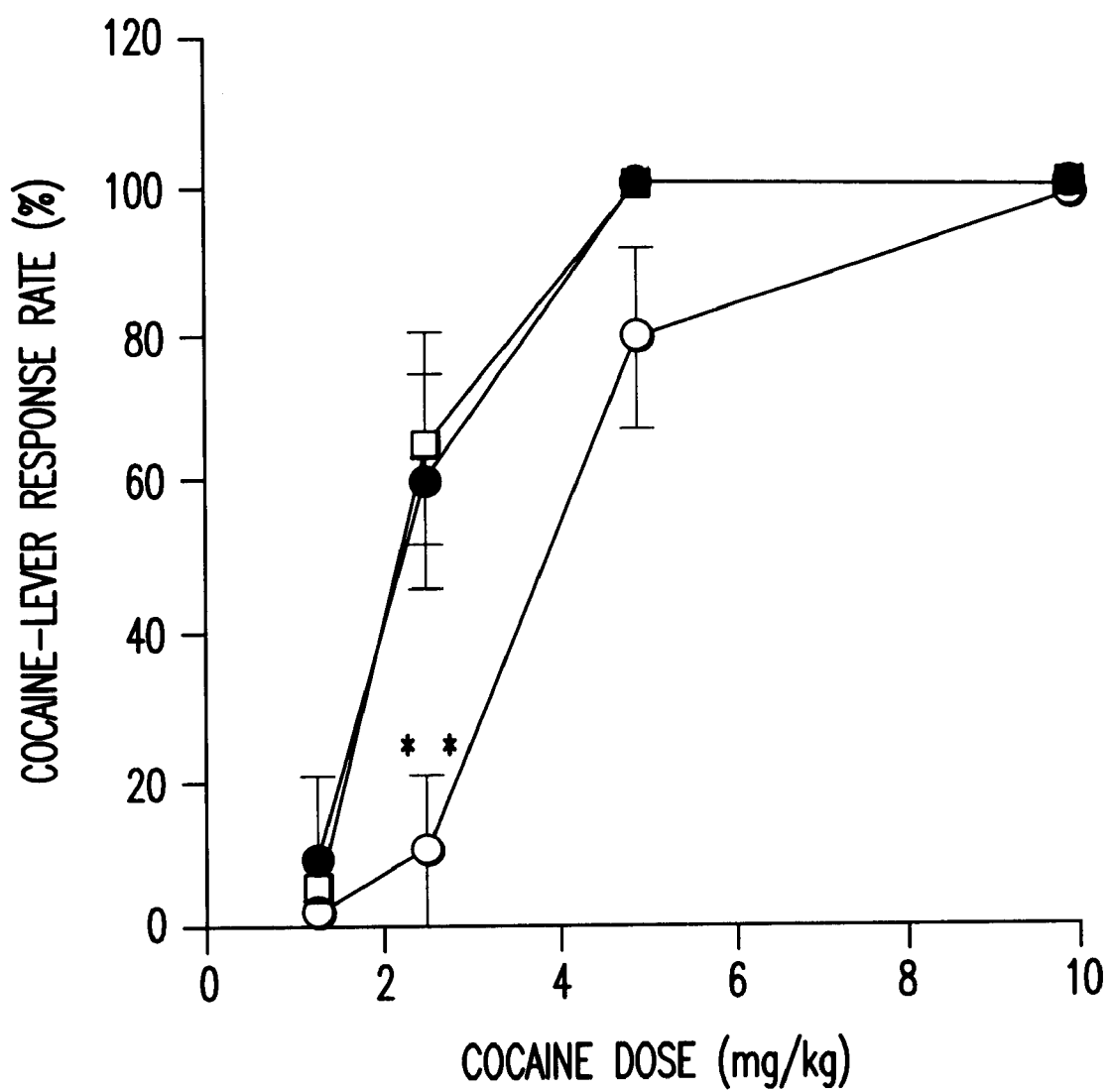
FIG. 9 shows an effect of an opioid κ receptor antagonist on an inhibition of cocaine discrimination by an opioid κ receptor agonist.

Furthermore, it was clear that when Compound 3 (20 μg/kg) was given in combination with cocaine (each dose), inhibitory effect of cocaine discrimination was enhanced compared with the case in which Compound 3 (10 μg/kg) was given. In addition, as shown in FIG. 9, when nor-BNI, that is, an opioid κ receptor antagonist was pretreated, rates of feeding behavior with lever pressing were same as those in the group given physiological saline in combination with cocaine. Thus, the inhibitory effect of cocaine discrimination of Compound 3 was antagonized by the opioid κ receptor antagonist. These results showed that the inhibitory effect of cocaine discrimination was manifested via the opioid κ receptor, so that psychic dependence induced by cocaine could be inhibited by the opioid κ receptor agonist.

In FIG. 9, a symbol ● represents the group which was given physiological saline in combination with cocaine, a symbol ○ represents the group which was given Compound 3 (0.02 mg/kg) in combination with cocaine, and a symbol □ represents the group which was given Compound 3 (0.02 mg/kg) in combination with cocaine after the pretreatment of nor-BNI. A symbol ** represents a level of significance of not more than 1%, thereby indicating statistical significance.

Example 7

Inhibitory effects on a mecamylamine-induced nicotine withdrawal syndrome by an opioid κ receptor agonist Animals used were SD strain male rats in this experiment. Experiments used were CPP operant boxes. Experiments were performed by using an aversive model in a nicotine withdrawal syndrome induced by mecamylamine, that is, a nicotine receptor antagonist. (Tsutomu Suzuki, Molecular Medicine, 32, 140 (1995); Suzuki, T. et al., Eur. J. Pharm., 314, 281 (1996); Maldonado, R. et al., J. Pharmacol. Exp. Ther., 261, 669 (1992)). Osmotic minipump (Alzet 2001, Alza Corporation) injected with nicotine (1 μl/hr, for seven days) was implanted under dorsal skin of the rats. An aqueous solution at a concentration of 121.4 mg/ml was prepared so that a nicotine dose was adjusted to 10 mg/kg/day. Then, the aqueous solution was filled into the osmotic minipump. The rats were given conditioning training by the following counter-balance method. In the morning of the seventh day after the implantation of the mini-osmotic pump, mecamylamine (1 mg/ml), that is, nicotine receptor antagonist or physiological saline was subcutaneously injected. Then, the rats were placed in one compartment for 60 minutes. And then, in the evening of the same day, the opposite treatments were performed (physiological saline was administered to the rats to which mecamylamine had been administered in the morning, and mecamylamine was administered to the rats to which physiological saline was administered in the morning), and the rats were placed in the other compartment for 60 minutes. Then, 17-(cyclopropylmethyl)-3,14β-dihydroxy-4,5α-epoxy-6β-[N-methyl-trans-3-(3-furyl)acrylamide] morphinan hydrochloride (Compound 3), that is, an opioid κ receptor selective agonist was subcutaneously administered 30 minutes before the mecamylamine treatment. On the next day of the conditioning training (the eighth day), tests were performed. The periods in which the rats remained in each compartment colored white or black were measured for 15 minutes.

Figure 10:
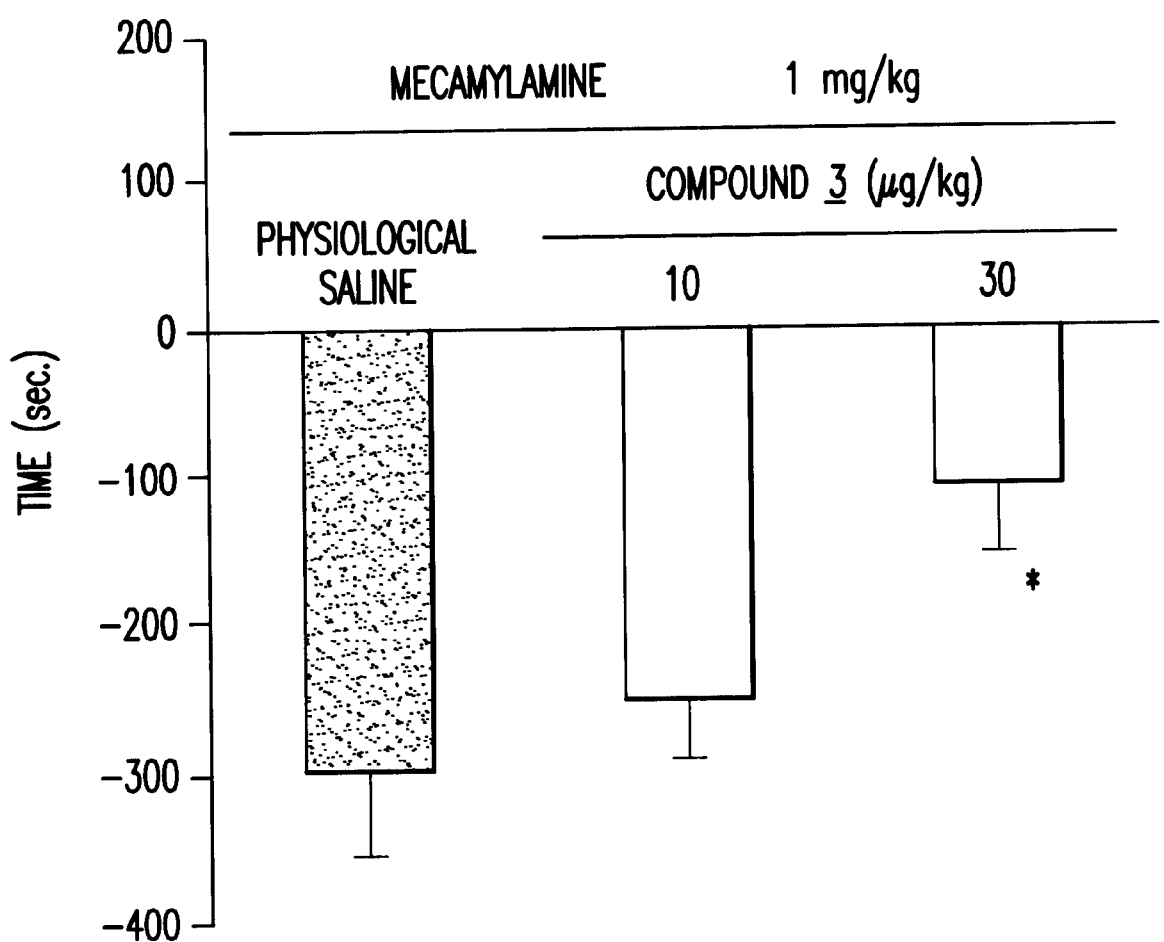
FIG. 10 shows inhibitory effects on a mecamylamine-induced nicotine withdrawal syndrome by an opioid κ receptor agonist.

The results were shown in FIG. 10. A negative value indicates the period in which rats escaped from the compartment conditioned by sucutaneous injection of mecamylamine. It was shown that the greater the negative value means the stronger the aversive effect at the nicotine withdrawal. The aversive effect induced by mecamylamine was inhibited by the pretreatment with Compound 3 (10 or 30 μg/kg) in a dose dependent manner. In addition, it was recognized that the pretreatment of Compound 3 (30 μg/kg) significantly inhibited the aversive effect compared with the aversive effect in the group pretreated with physiological saline. That is, the physical dependence developed by nicotine was inhibited.

In FIG. 10, a symbol * represents a level of significance of not more than 5%, thereby indicating statistical significance.

Example 8

Inhibitory effects on dopamine release by an opioid κ receptor agonist.

Animals used were SD strain male rats at an age of at least six weeks. After rats were killed by decapitation, the forebrains were enucleated. The forebrains were longitudinally severed in the mediad direction in Krebs-Ringer-Bicarbonate medium which were chilled in cracked ice, and sliced with a tissue chopper at intervals of 500 μm. The nucleus accumbens areas were knocked through the slices containing the nucleus accumbens using a punch having an inner diameter of 2 mm. After the nucleus accumbens were preincubated in the Krebs-Ringer-Bicarbonate medium under bubbling a gas containing $O_2$ at 95% and $CO_2$ at 5% for 20 minutes, they were placed in a reflux apparatus so as to be 24 slices per a chamber, and refluxed with the Krebs-Ringer-Bicarbonate medium which were added with nomifensine at a concentration of 10 μM for 30 minutes. Then, the reflux was performed at a rate of 0.25 ml/min. and samples were obtained at intervals of five minutes. After 20 minutes, and 60 minutes, 20 mM high $K^+$ stimulation were subjected for 10 minutes so as to facilitate dopanime release. 17 -(cyclopropylmethyl)-3,14β-dihydroxy-4,5α-epoxy-6β-[N-methyl-trans-3-(3-furyl)acrylamide] morphinan hydrochloride (Compound 3), that is, an opioid κ receptor agonist was dissolved in distilled water, diluted with the medium, and added 20 minutes before the second stimulus. The amounts of dopamine in the recovered samples were measured using a high-performance liquid chromatography-electron capture detector (HPLC-ECD) method at a flow rate of 0.25 ml/min, at a column temperature of 25° C., and at an applied voltage of 400 mV, in which a mobile phase was 0.1 M phosphate buffer (pH 6.0) and a Eicompak CA-50DS column (2.1φ×150 mm) attached by a precolumn was used.

Figure 11:
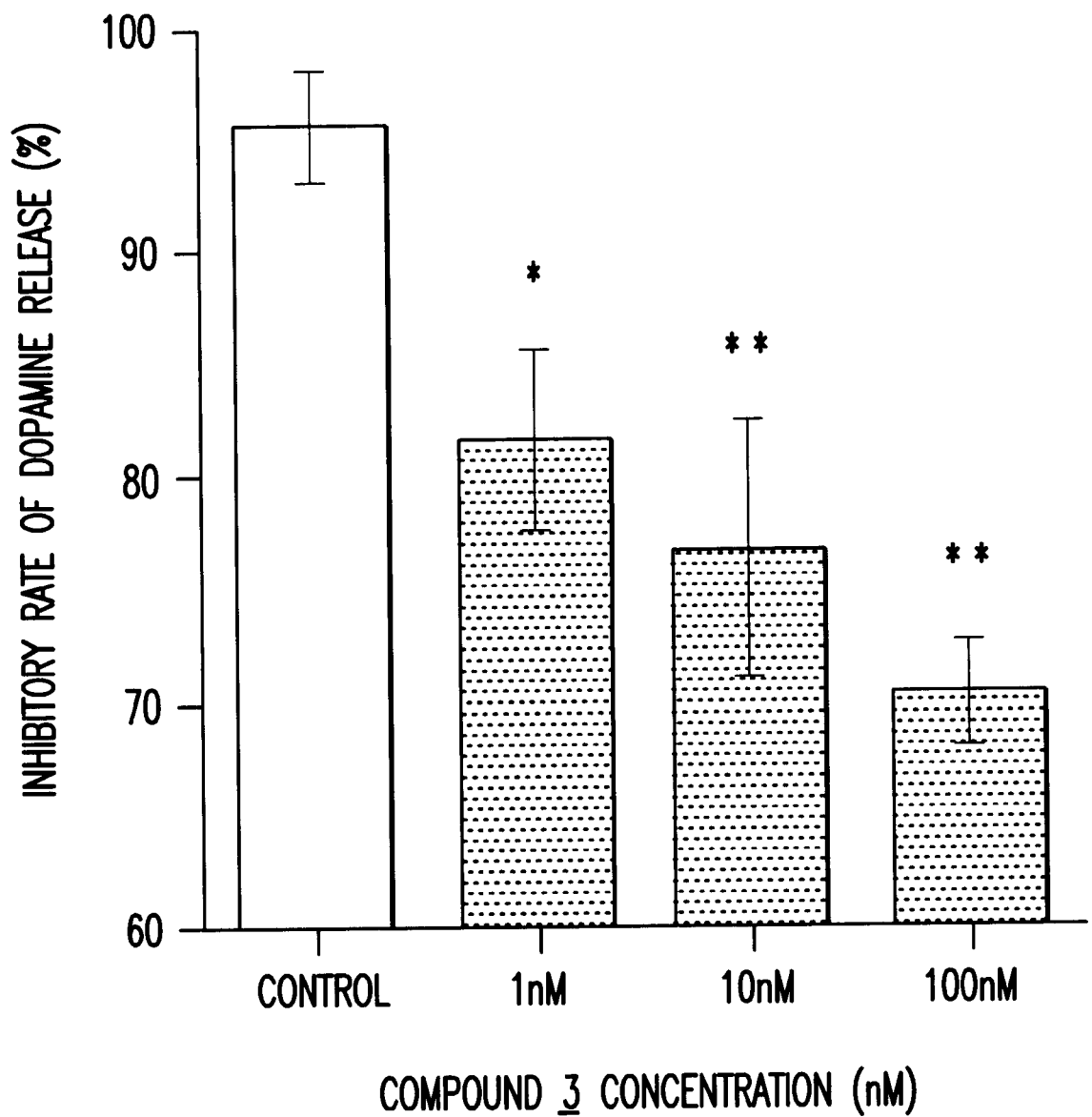
FIG. 11 shows inhibitory effects on dopamine release by an opioid κ receptor agonist.

The results were shown in FIG. 11. It was suggested that Compound 3 inhibited dopamine release in the nucleus accumbens projected form A10 nerve terminals which related to a drug reward effect.

Referring to FIG. 11, a symbol * represents a level of significance of not more than 5% and a symbol ** represents a level of significance of not more than 1%, thereby indicating statistical significance.

INDUSTRIAL APPLICABILITY

A remedy for drug dependence in accordance with the present invention is a promising medicament with reduced adverse effects, which inhibits development of psychic dependence, and also physical dependence by inhibiting reward effects induced by dependence-producing drugs.

What is claimed is:

1. A method for treating nicotine dependence, alcohol dependence, stimulant dependence, central nervous system sedative dependence, or hallucinogen dependence, which method comprises administering to a patient an opioid k receptor agonist represented by the following formula (I) or a pharmacologically acceptable acid-addition salt thereof:

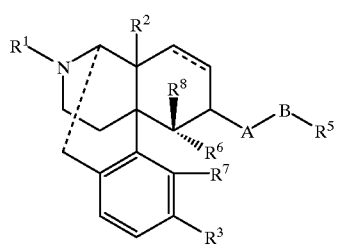

(I)

wherein

- - - - - is a double bond, or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophen-2-ylalkyl group having from 1 to 5 carbon atoms; $R^2$ is a hydrogen atom, a hydroxy group, a nitro group, an alkanoyloxy group having from 1 to 5 carbon atoms, an alkoxy group having from 1 to 5 carbon atoms, an alkyl group having from 1 to 5 carbon atoms, or $-NR^9R^{10}$; $R^9$ is a hydrogen atom or an alkyl group having from 1 to 5 carbon atoms; $R^{10}$ is a hydrogen atom, an alkyl group having from 1 to 5 carbon atoms, or $-C(=O)R^{11}$ is a hydrogen atom, a phenyl group, or an alkyl group having from 1 to 5 carbon atoms; $R^3$ is a hydrogen atom, a hydroxy group, an alkanoyloxy group having from 1 to 5 carbon atoms, or an alkoxy group having from 1 to 5 carbon atoms; A is $-XC(=Y)-$, $-XC(=Y)Z-$, $-X-$, or $-XSO_2-$, wherein X, Y and Z are, independently of one another, $NR^4$, S, or O; and $R^4$ is a hydrogen atom, a straight-chain or branched-chain alkyl group having from 1 to 5 carbon atoms, or an aryl group having from 6 to 12 carbon atoms; and $R^4$ is optionally identical or different in the formula; B is a valence bond, a straight-chain or branched-chain alkylene group having from 1 to 14 carbon atoms, wherein the alkylene group is optionally substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group, and wherein one to three methylene groups of the alkylene group is optionally replaced with carbonyl groups, a straight-chain or branched-chain acyclic unsaturated hydrocarbon containing from one to three double bonds and/or triple bonds and having from 2 to 14 carbon atoms, wherein the acyclic unsaturated hydrocarbon is optionally substituted by one or more substituents selected from the group consisting of an alkoxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group, and wherein one to three methylene groups of the acyclic unsaturated hydrocarbon is optionally replaced with carbonyl groups, or a straight-chain or branched-chain saturated or unsaturated hydrocarbon containing from one to five thioether, ether, and/or amino bonds and having from 1 to 14 carbon atoms, wherein no hetero atoms are bonded directly to A, and one to three methylene groups of the hydrocarbon is optionally replaced with carbonyl groups; and $R^5$ is a hydrogen atom or an organic group having a basic skeleton selected from the group consisting of the following formulas:

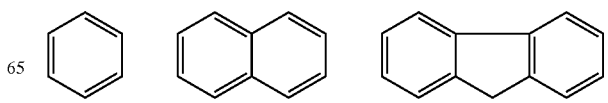

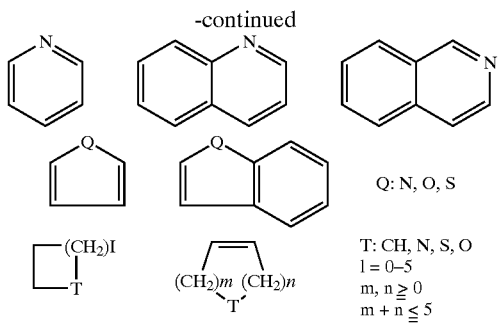

Q: N, O, S

T: CH, N, S, O
l = 0–5
m, n ≥ 0
m + n ≤ 5 wherein the organic group optionally has at least one substituent selected form the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; $R^6$ is a hydrogen atom; $R^7$ is a hydrogen atom, a hydroxy group, an alkoxy group having from 1 to 5 carbon atoms, or $R^6$ and $R^7$ are —O—, —CH$_2$—, —S— together; $R^8$ is a hydrogen atom, an alkyl group having from 1 to 5 carbon atoms or an alkanoyl group having from 1 to 5 carbon atoms.

2. The method for treating nicotine dependence of claim 1, wherein in the formula (I), $R^1$ is a methyl group, an ethyl group, a propyl group, a butyl group, an isobutyl group, a cyclopropylmethyl group, an allyl group, a benzyl group, or a phenethyl group; $R^2$ and $R^3$ are, independently of each other, a hydrogen atom, a hydroxy group, an acetoxy group, or a methoxy group; A is —XC(=Y)—, wherein X is NR$^4$, S, or O; Y is O; and $R^4$ is a hydrogen atom, or a straight-chain or branched-chain alkyl group having from 1 to 5 carbon atoms, —XC(=Y)Z—, —X—, or —XSO$_2$, wherein X is NR$^4$; Y is O or S; Z is NR$^4$ or O; and $R^4$ is a hydrogen atom, or a straight-chain or branched-chain alkyl group having from 1 to 5 carbon atoms; B is a straight-chain alkylene group having from 1 to 3 carbon atoms, —CH=CH—, —C≡C—, —CH$_2$O— or —CH$_2$S—; $R^5$ is as defined in claim 1; $R^6$ and $R^7$ are —O— together; and $R^8$ is a hydrogen atom.

3. The method for treating nicotine dependence of claim 2, wherein in the formula (I), A is —NR-4-C(=O)— or —NR—$^4$C(=O)O—, wherein R-4- is a hydrogen atom, or a straight-chain or branched-chain alkyl group having from 1 to 5 carbon atoms; B is a straight-chain alkylene group having from 1 to 3 carbon atoms, —CHαCH—, or —C≡C—; and $R^5$ is a hydrogen atom or an organic group having a basic skeleton selected from the group consisting of the following formulas:

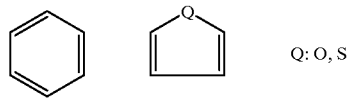

Q: O, S wherein the organic group optionally has at least one substituent selected from the group consisting of an alkyl group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group.

4. A method for treating cocaine dependence which comprises administering an opioid k receptor agonist, or a pharmacologically acceptable acid-addition salt thereof, to a patient who is dependent on cocaine, wherein said opioid k receptor agonist is represented by the following formula (I):

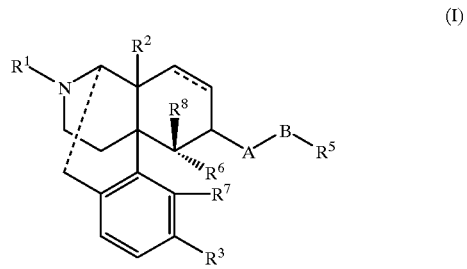

(I)

wherein

----- is a double bond, or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophen-2-ylalkyl group having from 1 to 5 carbon atoms; $R^2$ is a hydrogen atom, a hydroxy group, a nitro group, an alkanoyloxy group having from 1 to 5 carbon atoms, an alkoxy group having from 1 to 5 carbon atoms, or —NR$^9$R$^{10}$; $R^9$ is a hydrogen atom or an alkyl group having from 1 to 5 carbon atoms; $R^{10}$ is a hydrogen atom, an alkyl group having from 1 to 5 carbon atoms; $R^3$ is a hydrogen atom, a hydroxy group, an alkanoyloxy group having from 1 to 5 carbon atoms, or an alkoxy group having from 1 to 5 carbon atoms; A is —XC(=Y)—, —XC(=Y)Z—, —X—, or —XSO$^2$, wherein X, Y and Z are, independently of one another, NR$^4$S, or O; and $R^4$ is a hydrogen atom, a straight-chain or branched-chain alkyl group having from 1 to 5 carbon atoms; and $R^4$ is optionally identical or different in the formula; B is a valence bond, a straight-chain or branched-chain alkylene group having from 1 to 14 carbon atoms, wherein the alkylene group is optionally substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, ad a phenoxy group, and wherein one to three methylene groups of the alkylene group is optionally replaced with carbonyl groups, straight-chain or branched-chain acyclic unsaturated hydrocarbon containing from one to three double bonds and/or triple bonds and having from 2 to 14 carbon atoms, wherein the acyclic unsaturated hydrocarbon is optionally substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group, and wherein one to three methylene groups of the acyclic unsaturated hydrocarbon is optionally replaced with carbonyl groups, or a straight-chain or branched-chain saturated or unsaturated hydrocarbon containing from one to five thioether, ether, and/or amino bonds and having from 1 to 14 carbon atoms, wherein no hetero atoms are bonded directly to A, and one to three methylene groups of the hydrocarbon is optionally replaced with carbonyl groups; and $R^5$ is a hydrogen atom or an organic group having a basic skeleton selected from the group consisting of the following formulas:

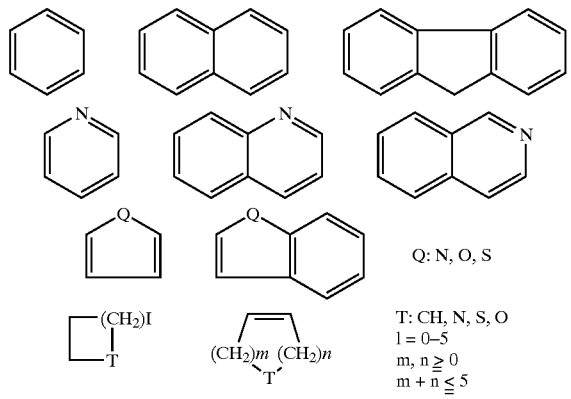

wherein the organic group optionally has at least one substituent selected from the group consisting of an alkyl group having from 1 to 5 carbon atoms, an alkoxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; $R^6$ is a hydrogen atom; $R^7$ is a hydrogen atom, a hydroxy group, an alkoxy group having from 1 to 5 carbon atoms, or an alkanoyloxy group having from 1 to 5 carbon atoms, or $R^6$ and $R^7$ are —O—, —$CH_2$—, —S— together; $R^8$ is a hydrogen atom, an alkyl group having from 1 to 5 carbon atoms or an alkanoyl group having from 1 to 5 carbon atoms.

5. The method for treating cocaine dependence of claim 4, wherein in the general formula (I), $R^1$ is a methyl group, an ethyl group, a propyl group, a butyl group, an isobutyl group, a cyclopropylmethyl group, an allyl group, a benzyl group, or a phenethyl group; $R^2$ and $R^3$ are, independently of each other, a hydrogen atom, a hydroxy group, an acetoxy group, or a methoxy group; A is —XC(=Y)—, wherein X is $NR^4$, S, or O; Y is O; and $R^4$ is a hydrogen atom, or a straight-chain atoms, —XC(=Y)Z—, —X—, or —$XSO_2$—, wherein X is $NR^4$; Y is O or S; X is $NR^4$ or O; and $R^4$ is a hydrogen atom, or a straight-chain or branched-chain alkyl group having from 1 to 5 carbon atoms; B is a straight-chain alkylene group having from 1 to 3 carbon atoms, —CH=CH—, —C≡C—, —$CH_2$O— or $CH_2$S—; $R^5$ is the same as that in claim 4; $R^6$ and $R^7$ are —O— together; and $R^8$ is a hydrogen atom.

6. The method for treating cocaine dependence of claim 5, wherein in the formula (I), A is —$NR^4C$(=O)— or —$NR^4C$(=O)O, wherein $R^4$ is a hydrogen atom, or a straight-chain or branched-chain alkyl group having from 1 to 5 carbon atoms; B is a straight-chain alkylene group having from 1 to 3 carbon atoms, —CH=CH—, or —C≡C—; and $R^5$ is a hydrogen atom or an organic group having a basic skeleton selected from the group consisting of the following formulas:

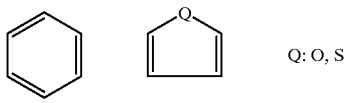

wherein the organic group optionally has at least one substituent selected from the group consisting of an alkyl group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group.

7. A method of treating opioid μ receptor agonist dependence which comprises administering an opioid k receptor agonist or a pharmacologically acceptable acid-addition salt thereof, wherein said derivative is represented by the following formula (I):

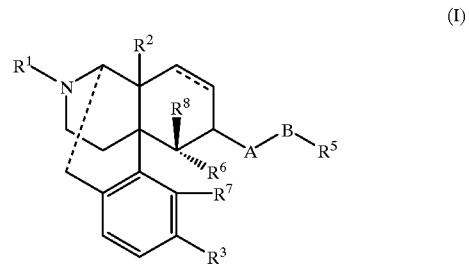

wherein

----- is a double bond, or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophen-2-ylalkyl group having from 1 to 5 carbon atoms; $R^2$ is a hydrogen atom, a hydroxy group, a nitro group, an alkanoyloxy group having from 1 to 5 carbon atoms, an alkoxy group having from 1 to 5 carbon atoms, an alkyl group having from 1 to 5 carbon atoms, or —$NR^9R^{10}$; $R^9$ is a hydrogen atom or an alkyl group having from 1 to 5 carbon atoms; $R^{10}$ is a hydrogen atom, an alkyl group having from 1 to 5 carbon atoms; $R^{10}$ is a hydrogen atom, an alkyl group having from 1 to 5 carbon atoms, or —C(=O)$R^{11}$ is a hydrogen atom, a hydroxy group, an alkanoyloxy group having from 1 to 5 carbon atoms; A is —XC(=Y)—, —XC(=Y)Z—, —X—, or —$XSO_2$—, wherein X, Y and Z are, independently of one another, $NR^4$, S, or O; and $R^4$ is a hydrogen atom, a straight-chain or branched-chain alkyl group having from 1 to 5 carbon atoms, or an aryl group having from 6 to 12 carbon atoms; and $R^4$ is optionally identical or different in the formula; B is a valence bond, a straight-chain or branched-chain alkylene group having from 1 to 14 carbon atoms, wherein the alkylene group is optionally substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group, and wherein one to three methylene groups of the alkylene group is optionally replaced with carbonyl groups, a straight-chain or branched-chain acyclic unsaturated hydrocarbon containing from one to three double bonds and/or triple bonds and having from 2 to 14 carbon atoms, wherein the acyclic unsaturated hydrocarbon is optionally substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group and wherein one to three methylene groups of the acyclic unsaturated hydrocarbon is optionally replaced with carbonyl groups, or a straight-chain or branched-chain saturated or unsaturated hydrocarbon containing from one to five thioether, ether, and/or amino bonds and having from 1 to 14 carbon atoms, wherein no hetero atoms are bonded directly to A, and one to three methylene groups of the hydrocarbon is optionally replaced with carbonyl groups; and $R^5$ is a hydrogen atom or an organic group having a basic skeleton selected from the group consisting of the following formulas:

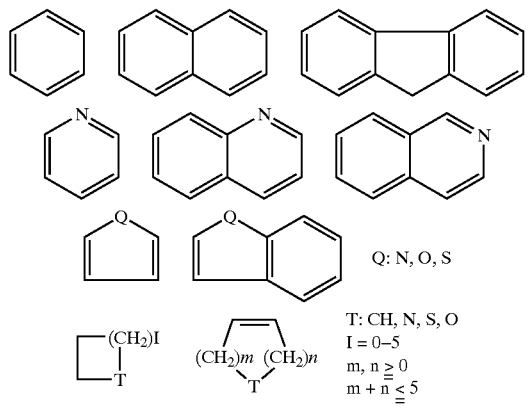

wherein the organic group optionally has at least one substituent selected from the group consisting of an alkyl group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; $R^6$ is a hydrogen atom; $R^7$ is a hydrogen atom, a hydroxy group, an alkoxy group having from 1 to 5 carbon atoms, or an alkanoyloxy group having from 1 to 5 carbon atoms, or $R^6$ and $R^7$ are —O—, —CH$_2$—, —S— together; $R^8$ is a hydrogen atom, an alkyl group having from 1 to 5 carbon atoms or an alkanoyl group having from 1 to 5 carbon atoms.

8. The method for treating opioid $\mu$ receptor agonist dependence of claim 7, wherein in the formula (I), $R^1$ is a methyl group, an ethyl group, a propyl group, a butyl group, an isobutyl group, a cyclopropylmethyl group, an allyl group, a benzyl group, or a phenethyl group; $R^2$ and $R^3$ are, independently of each other, a hydrogen atom, a hydroxy group, an acetoxy group, or a methoxy group; A is —XC (Y=)—, wherein X is NR$^4$, S, or O; Y is O; and $R^4$ is a hydrogen atom, or a straight-chain or branched-chain alkyl group having from 1 to 5 carbon atoms, —XC(=Y)Z—, —X—, or —XSO$_2$—, wherein X is NR$^4$ Y is O or S; Z is NR$^4$ or O; and $R^4$ is a hydrogen atom, or a straight-chain or branched-chain alkyl group having from 1 to 5 carbon atoms; B is a straight-chain alkylene group having from 1 to 3 carbon atoms, —CH=CH—, —C≡C—, —CH$_2$O— or —CH$_2$S—; $R^5$ is the same as that in claim 7; $R^6$ and $R^7$ are —O— together; and $R^8$ is a hydrogen atom.

9. The method for treating opioid $\mu$ receptor agonist dependence of claim 8, wherein in the formula (I), A is —NR$^4$C(=O)— or —NR$^4$C(=O)O—, wherein $R^4$ is a hydrogen atom, or a straight-chain or branched-chain alkyl group having from 1 to 5 carbon atoms; B is a straight-chain alkylene group having from 1 to 3 carbon atoms, —CH=CH—, or —C≡C—; and $R^5$ is a hydrogen atom or an organic group having a basic skeleton selected from the group consisting of the following formulas:

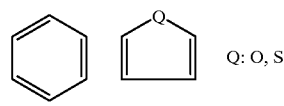

wherein the organic group optionally has at least one substituent selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group.

10. A method of inhibiting dopamine release which comprises administering an opioid K agonistic morphinan derivative or a pharmacologically acceptable acid-addition salt thereof, wherein said derivative is represented by the following formula (I):

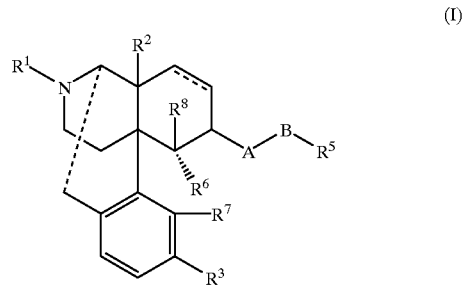

wherein is a double bond, or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophen-2-ylalkyl group having from 1 to 5 carbon atoms; $R^2$ is a hydrogen atoms, a hydroxy group, a nitro group, an alkanoyloxy group having from 1 to 5 carbon atoms, an alkoxy group having from 1 to 5 carbon atoms, an alkyl group having from 1 to 5 carbon atoms, or —NR⁹R¹⁰; R⁹ is a hydrogen atom or an alkyl group having from 1 to 5 carbon atoms; R¹⁰ is a hydrogen atom, an alkyl group having from 1 to 5 carbon Atoms, or —C(=O)R¹¹; R¹¹ is a hydrogen atom, a phenyl group, or an alkyl group having from 1 to 5 carbon atoms; R³ is a hydrogen atom, a hydroxy group, an alkanoyloxy group having from 1 to 5 carbon atoms, or an alkoxy group having from 1 to 5 carbon atoms; A is —XC(=Y)Z—, —X—, or —XSO₂—, wherein X, Y and Z are, independently of one another, NR⁴, S, or O; and R⁴ is a hydrogen atom, a straight-chain or branched-chain alkyl group having from 1 to 5 carbon atoms, or an aryl group having from 6 to 12 carbon atoms; and R⁴ is optionally identical or different in the formula; B is a valence bond, a straight-chain or branched-chain alkylene group having from 1 to 14 carbon atoms, wherein the alkylene group is optionally substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group, and wherein one to three methylene groups of the alkylene group is optionally replaced with carbonyl groups, a straight-chain or branched-chain acyclic unsaturated hydrocarbon containing from one to three double bonds and/or triple bonds and having from 2 to 14 carbon atoms, wherein the acyclic unsaturated hydrocarbon is optionally substituted by one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group, and a phenoxy group, and wherein one to three methylene groups of the acyclic unsaturated hydrocarbon is optionally replaced with carbonyl groups, or straight-chain or branched-chain saturated or unsaturated hydrocarbon containing from one to five thioether, ether, and/or amino bonds and having from 1 to 14 carbon atoms, wherein no hetero atoms are bonded directly to A, and one to three methylene groups of the hydrocarbon is optionally replaced with carbonyl groups; and R⁵ is a hydrogen atom or an organic group having a basic skeleton selected from the group consisting of the following formulas:

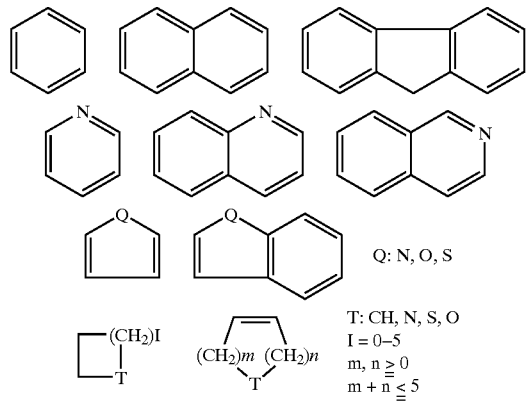

wherein the organic group optionally has at least one substituent selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; R⁶ is a hydrogen atom; R⁷ is a hydrogen atom, a hydroxy group, an alkoxy group having from 1 to 5 carbon atoms, or an alkanoyloxy group having from 1 to 5 carbon atoms, or R⁶ and R⁷ are —O—, —CH₂—, —S— together; R⁸ is a hydrogen atom, an alkyl group having from 1 to 5 carbon atoms, or an alkanoyl group having from 1 to 5 carbon atoms.

11. The method of inhibiting dopamine-release of claim 10, wherein in the formula (I), R¹ is a methyl group, an ethyl group, a propyl group, a butyl group, an isobutyl group, a cyclopropylmethyl group, an allyl group, a benzyl group, or a phenethyl group; R² and R³ are, independently of each other, a hydrogen atom, a hydroxy group, an acetoxy group, or a methoxy group; A is —XC(=Y)—, wherein X is NR⁴, S, or O; Y is O; and R⁴ is a hydrogen atom, or a straight-chain or branched-chain alkyl group having from 1 to 5 carbon atoms, —XC(=Y)Z—, —X—, or —XSO₂—, wherein X is NR⁴; Y is O or S; Z is NR⁴ or O; and R⁴ is a hydrogen atom, or a straight-chain or branched-chain alkyl group having from 1 to 5 carbon atoms; B is a straight-chain alkylene group having from 1 to 3 carbon atoms, —CH=CH—, CH₂O— or —CH₂S—; R⁵ is the same as that in claim 10; R⁶ and R⁷ are —O— together; and R⁸ is a hydrogen atom.

12. The method of inhibiting dopamine-release inhibitor of claim 11, wherein in the formula (I), A is —NR⁴C(=O)— or —NR⁴C(=O)O—, wherein R⁴ is a hydrogen atom, or a straight-chain or branched-chain alkyl group having from 1 to 5 carbon atoms; B is a straight-chain alkylene group having from 1 to 3 carbon atoms, —CH=CH—, or —C=C—; and R⁵ is a hydrogen atom or an organic group having a basic skeleton selected from the group consisting of the following formulas:

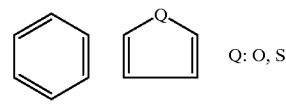

wherein the organic group optionally has at last one substituent selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group.

13. The method of inhibiting dopamine-release of claim 12, wherein diseases to be treated include nicotine dependence, cocaine dependence, opioid μ receptor agonist dependence, alcohol dependence, stimulant dependence, central nervous system sedative dependence, and hallucinogen dependence.

* * * * *